US010080387B2

(12) United States Patent
Phillips et al.

(10) Patent No.: US 10,080,387 B2
(45) Date of Patent: Sep. 25, 2018

(54) AEROSOL DELIVERY DEVICE WITH REPLACEABLE WICK AND HEATER ASSEMBLY

(71) Applicant: RAI Strategic Holdings, Inc., Winston-Salem, NC (US)

(72) Inventors: Percy D. Phillips, Pfafftown, NC (US); James William Rogers, Winston-Salem, NC (US); Lisa E. Brown, Lexington, NC (US); James Demopoulos, Winston-Salem, NC (US); Michael F. Davis, Clemmons, NC (US); Noah Mark Minskoff, Palo Alto, CA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 10 days.

(21) Appl. No.: 15/274,073

(22) Filed: Sep. 23, 2016

(65) Prior Publication Data

US 2018/0084828 A1    Mar. 29, 2018

(51) Int. Cl.
*A24F 13/00* (2006.01)
*A24F 47/00* (2006.01)
*H05B 1/02* (2006.01)
*A61M 15/06* (2006.01)
*A61M 15/00* (2006.01)

(52) U.S. Cl.
CPC ....... *A24F 47/008* (2013.01); *A61M 15/0021* (2014.02); *A61M 15/06* (2013.01); *H05B 1/0244* (2013.01); *A61M 2205/36* (2013.01); *H05B 2203/021* (2013.01)

(58) Field of Classification Search
CPC .................................................. A24F 47/008
USPC ........................................................ 131/329
See application file for complete search history.

(56) References Cited

U.S. PATENT DOCUMENTS

| | | |
|---|---|---|
| 1,771,366 A | 7/1930 | Wyss et al. |
| 2,057,353 A | 10/1936 | Whittemore, Jr. |
| 2,104,266 A | 1/1938 | McCormick |
| 3,200,819 A | 8/1965 | Gilbert |
| 4,284,089 A | 8/1981 | Ray |

(Continued)

FOREIGN PATENT DOCUMENTS

| | | |
|---|---|---|
| AU | 276250 | 7/1965 |
| CA | 2 641 869 | 5/2010 |

(Continued)

*Primary Examiner* — Tulsidas C Patel
*Assistant Examiner* — Peter G Leigh
(74) *Attorney, Agent, or Firm* — Womble Bond Dickinson (US) LLP

(57) ABSTRACT

An aerosol delivery device includes a housing and a reservoir having an open end and an opposing closed end. The reservoir includes an aerosol precursor composition therein. The aerosol delivery device also includes an electrical contact in or on the housing. The device further includes a vaporizing unit. The vaporizing unit includes a liquid transport element, a heating element, and an electrical connector. The vaporizing unit is configured to removably engage the open end of the reservoir such that the liquid transport element is in arrangement with the reservoir to transfer the aerosol precursor composition from the reservoir to the heating element and configured to engage the electrical contact in or on the housing.

23 Claims, 15 Drawing Sheets

(56) References Cited

U.S. PATENT DOCUMENTS

| | | | |
|---|---|---|---|
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiling et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,637,430 B1* | 10/2003 | Voges .............. A61M 15/0065 128/200.14 |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0031968 A1 | 2/2010 | Sheikh et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0074857 A1* | 3/2013 | Buchberger .......... A61M 15/06 131/329 |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0298905 A1 | 11/2013 | Levin et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0014125 A1* | 1/2014 | Fernando .............. A24F 47/008 131/328 |
| 2014/0041655 A1* | 2/2014 | Barron ................. A61M 11/042 128/202.21 |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |

(56) References Cited

U.S. PATENT DOCUMENTS

| | | |
|---|---|---|
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0290650 A1* | 10/2014 | Ivey ............... A24F 47/008 128/202.21 |
| 2014/0345631 A1 | 11/2014 | Bowen et al. |
| 2015/0053217 A1 | 2/2015 | Steingraber et al. |
| 2015/0245656 A1* | 9/2015 | Memari ............ A24F 15/12 206/242 |
| 2015/0245657 A1* | 9/2015 | Memari ............ A24F 15/12 141/18 |
| 2016/0050975 A1* | 2/2016 | Worm ............... A24F 47/008 131/328 |
| 2016/0073695 A1* | 3/2016 | Sears ............... H05B 3/46 131/329 |
| 2016/0150824 A1* | 6/2016 | Memari ............ A24F 15/12 131/329 |
| 2016/0192713 A1* | 7/2016 | Memari ............ A24F 15/12 141/2 |
| 2016/0262453 A1* | 9/2016 | Ampolini ......... H05B 3/0033 |
| 2016/0345629 A1 | 12/2016 | Mironov |
| 2016/0345636 A1 | 12/2016 | Liu |
| 2017/0055586 A1 | 3/2017 | Liu |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2015/165086 | 11/2015 |

\* cited by examiner

AEROSOL DELIVERY DEVICE WITH REPLACEABLE WICK AND HEATER ASSEMBLY

FIELD OF THE DISCLOSURE

The present disclosure relates to aerosol delivery devices such as smoking articles, and more particularly, to aerosol delivery devices that may utilize electrically generated heat for the production of aerosol (e.g., smoking articles commonly referred to as electronic cigarettes). The smoking articles may be configured to heat an aerosol precursor composition, which may incorporate materials that may be made or derived from tobacco or otherwise incorporate tobacco, the aerosol precursor composition capable of forming an inhalable substance for human consumption.

BACKGROUND

Many smoking devices have been proposed throughout the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices, aerosol precursor compositions, and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al.; 2014/0283859 to Minskoff et al.; 2015/0335070 to Sears et al.; 2015/0335071 to Brinkley et al.; 2016/0007651 to Ampolini et al.; 2016/0050975 to Worm et al.; all of which are incorporated herein by reference.

Certain existing embodiments of aerosol delivery devices include a control body (i.e., a power source assembly) and a cartridge (i.e., a reservoir housing). A power source (e.g., a battery) may be positioned in the control body, and an aerosol precursor composition may be retained and/or stored within the cartridge. The cartridge and the control body may engage one another to define an elongated tubular configuration. However, certain other form factors for aerosol delivery devices and other aerosol precursor composition storage arrangements may be desirable.

BRIEF SUMMARY OF THE DISCLOSURE

The present disclosure relates to materials and combinations thereof useful in aerosol delivery devices (e.g., electronic smoking articles) and like personal devices. In particular, the present disclosure relates to reservoirs that may be included in aerosol delivery devices and/or methods of assembling an aerosol delivery device with a reservoir.

In various aspects, the present disclosure provides an aerosol delivery device that includes a housing and a reservoir having an open end and an opposing closed end. The reservoir is configured to retain an aerosol precursor composition therein. Additionally, the aerosol delivery device includes an electrical contact in or on the housing. The aerosol delivery device includes a vaporizing unit that includes a liquid transport element, a heating element and an electrical connector. The vaporizing unit is configured to removably engage the open end of the reservoir such that the liquid transport element is in an arrangement with the reservoir to transfer the aerosol precursor composition form the reservoir to the heating element. Further, the vaporizing unit is configured to engage the electrical contact in or on the housing.

According to some aspects, the aerosol delivery device may include a power source disposed within the housing. The power source may be configured to provide an electrical current to the heating element when the vaporizing unit is engaging the open end of the reservoir and disposed in an operating position. The aerosol delivery device may further include a mouthpiece coupleably engaged with the vaporizing unit.

In some aspects, the mouthpiece may be configured to receive an electrical current from the power source when the mouthpiece is coupleably engaged with the vaporizing unit and the vaporizing unit is engaged with the open end of the reservoir. The power source may be configured to provide an electrical current to the heating element when the mouthpiece is coupleably engaged with the vaporizing unit disposed in the operating position.

According to some aspects, the vaporizing unit may include an outer shell. The outer shell may define an aperture proximate a first end of the outer shell and an annular channel proximate an opposing second end of the outer shell. Additionally, the heating element and the liquid transport element may be disposed within the outer shell. In some aspects, the housing may further include an engaging element configured to operably engage the annular channel when the vaporizing unit is disposed in the operating position. The engaging element may include the electrical contact. In some aspects, the mouthpiece coupleably engaged with the vaporizing unit may be configured to receive an electrical current from the power source when the electrical connector of the vaporizing unit is engaged with the electrical contact in or on the housing.

In some aspects, the aerosol delivery device includes a sealing element disposed proximate the open end of the reservoir. The vaporizing unit may be sealably engaged with the sealing element when the vaporizing unit is disposed in the operating position. According to some aspects, the sealing element may be configured to retain the aerosol precursor composition within the reservoir when the vaporizing unit is removably disengaged from the open end of the reservoir. Additionally, the sealing element may be configured to remove excess aerosol precursor composition from the vaporizing unit as the vaporizing unit traverses the sealing element and is removably disengaged from the open end of the reservoir.

According to some aspects, the housing may define a fill orifice that is in fluid communication with the open end of the reservoir. The aerosol delivery device may further include a filling orifice engaging element configured to removably and sealably engage a container for filling the reservoir with the aerosol precursor composition.

The present disclosure may also provide for an aerosol delivery device that includes a housing that has a reservoir. The reservoir is configured to retain an aerosol precursor composition therein. Additionally, the aerosol delivery device includes a removable vaporizing unit configured to engage the reservoir, and a mouthpiece that is coupleably engaged with the vaporizing unit. Further, the housing, vaporizing unit, and the mouthpiece collectively form an electrical circuit.

According to some aspects, the aerosol delivery device may further include at least one electrical contact in or on the housing. In some aspects, the electrical contact is in electrical connection with the circuit. Additionally or alternatively, the mouthpiece may be configured to coupleably engage the vaporizing unit to form the electrical circuit. According to one aspect, the mouthpiece may be configured to engage the at least one electrical contact to form the electrical circuit. In some aspects, the aerosol delivery device may further include a power source, and the vaporizing unit may include a liquid transport element and a heating element. The power source may be configured to provide an electrical current to the heating element through the electrical circuit when the housing, vaporizing unit, and the mouthpiece are coupleably engaged with one another.

The present disclosure may also provide for an aerosol delivery device that includes a housing and a reservoir disposed in or on the housing. The reservoir includes an open end and an opposing closed end and is configured to retain an aerosol precursor composition therein. The aerosol delivery device further includes an electrical contact in or on the housing and a power source disposed within the housing. The power source is in electrical connection with the electrical contact. Additionally, the aerosol delivery device includes a controller disposed within the housing. The controller is configured to control the electrical current provided by the power source to the electrical contact.

The aerosol delivery device may further include a vaporizing unit, which may be configured to removably engage the open end of the reservoir such that a liquid transport element of the vaporizing unit is arranged with respect to the reservoir to transfer the aerosol precursor composition from the reservoir to a heating element within the vaporizing unit when the vaporizing unit is disposed in an operating position. The aerosol delivery device may further include a mouthpiece coupleably engaged with the vaporizing unit.

According to some aspects, the power source is configured to provide an electrical current to the heating element and to electrically communicate with the mouthpiece when the mouthpiece is coupleably engaged with the vaporizing unit and the vaporizing unit is disposed in the operating position. The aerosol delivery device may further include an engaging element within the housing. The engaging element may be configured to operably engage an annular channel defined by an outer shell of the vaporizing unit when the vaporizing unit is disposed in the operating position. In some aspects, the engaging element may include the electrical contact in or on the housing.

In one or more embodiments, the aerosol delivery device can be configured such that the reservoir removably engages the housing. For example, the reservoir can be a self-contained unit that can be inserted into the housing or can be attached to the housing. In some embodiments, the reservoir can be positioned adjacent an outer wall of the housing. For example, the housing can be configured such that an outer wall of the housing includes a horizontal portion and a connected vertical portion—e.g., the horizontal portion and the vertical portion can be substantially at a 90 degree angle relative to one another. In this manner, the reservoir can include a bottom wall and a side wall, and the bottom wall of the reservoir can be configured to engage the horizontal portion of the housing wall, and the side wall of the reservoir can be configured to engage the vertical portion of the housing wall. In some embodiments, the outer wall of the housing (e.g., the above-noted horizontal portion and/or vertical portion) can include a light source configured to illuminate the reservoir.

These and other features, aspects, and advantages of the disclosure will be apparent from a reading of the following detailed description together with the accompanying drawings, which are briefly described below.

BRIEF DESCRIPTION OF THE DRAWINGS

Figure 1:
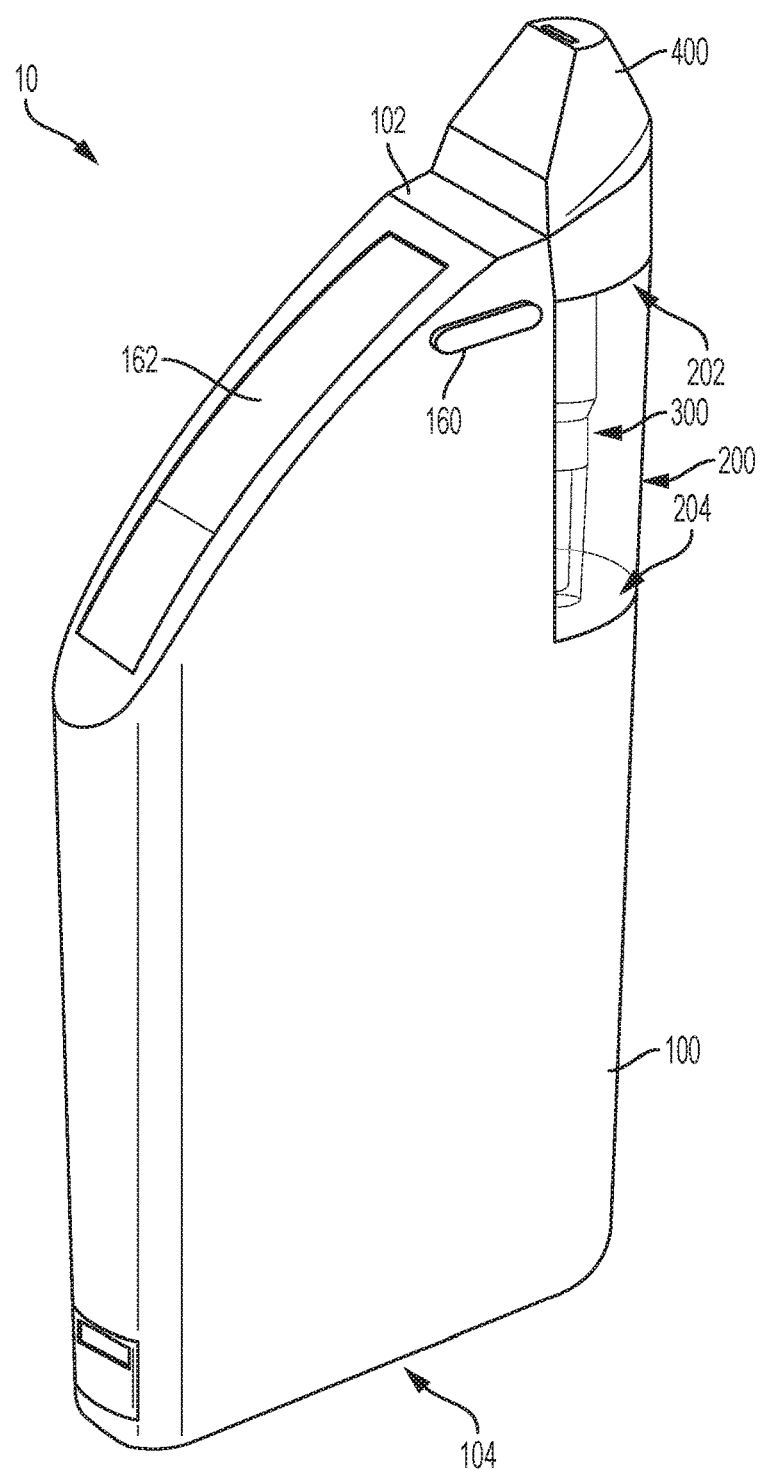
Figure 2:
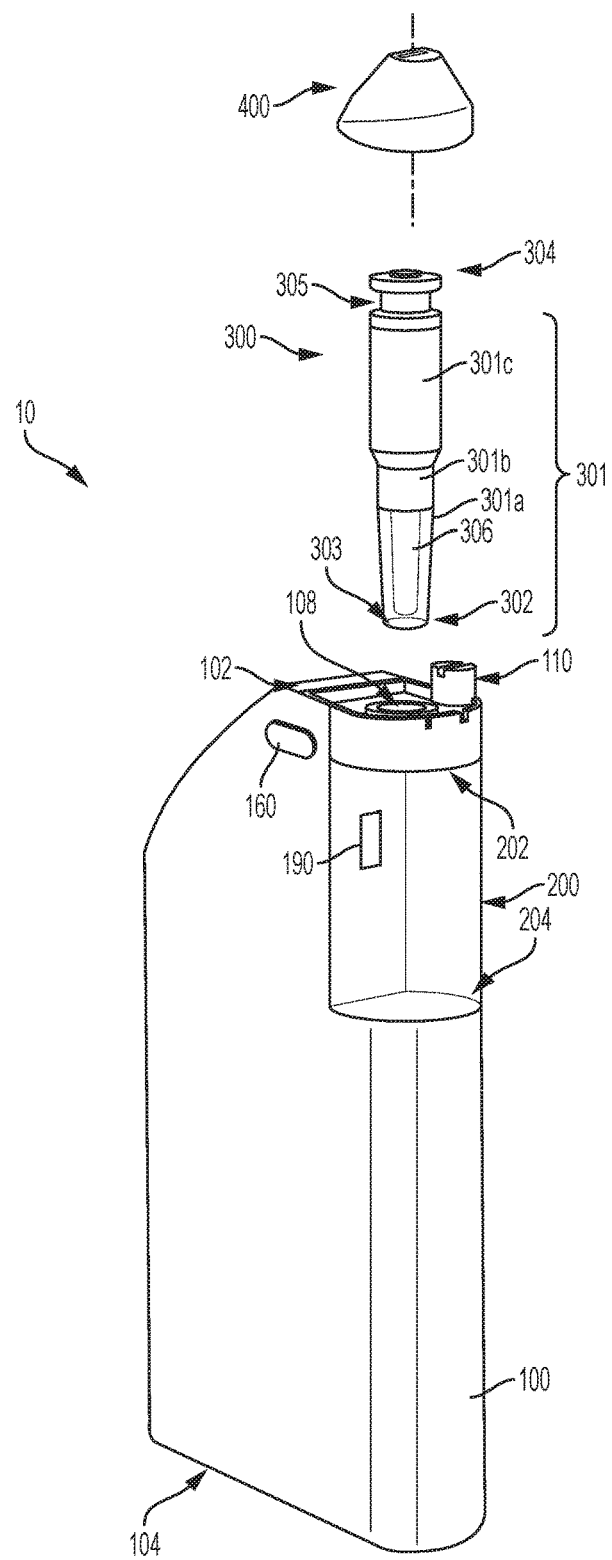
Figure 3A:
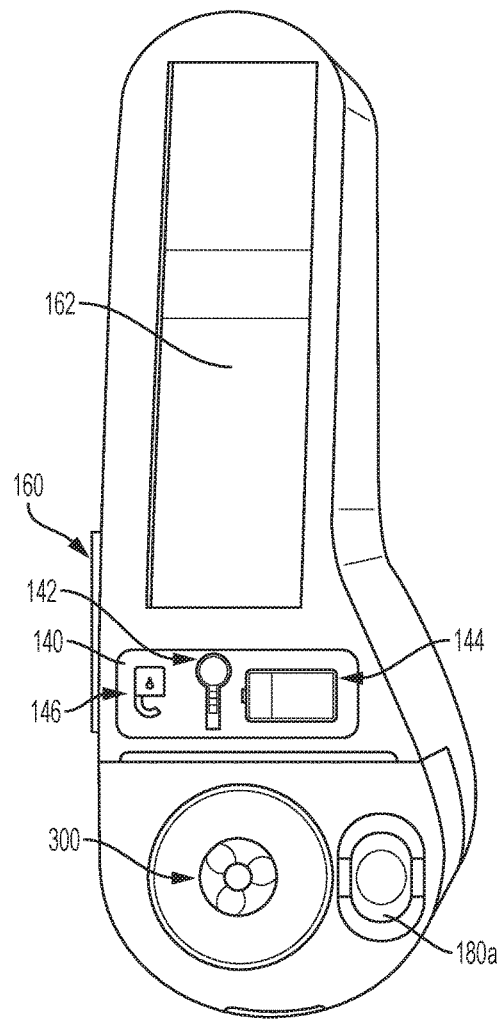
Figure 3B:
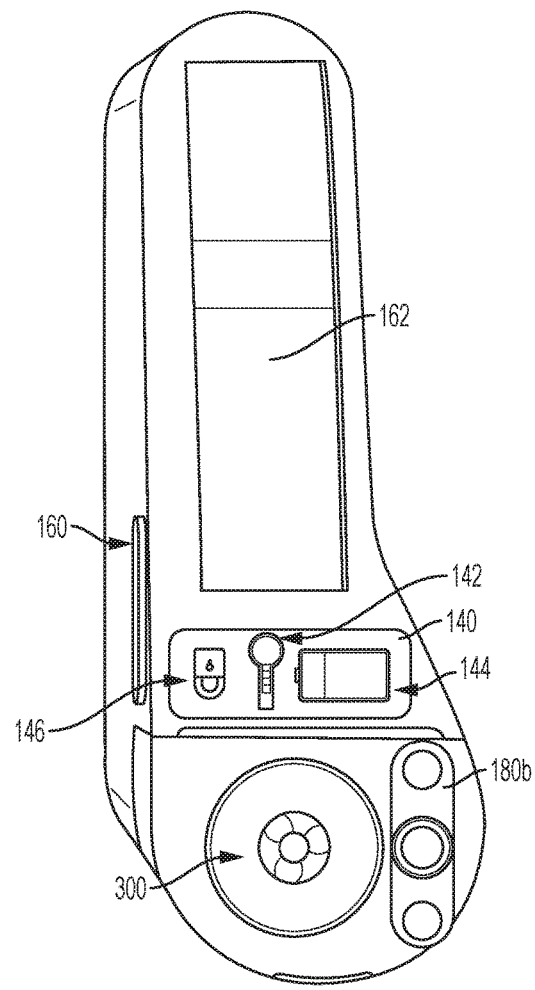
Figure 4A:
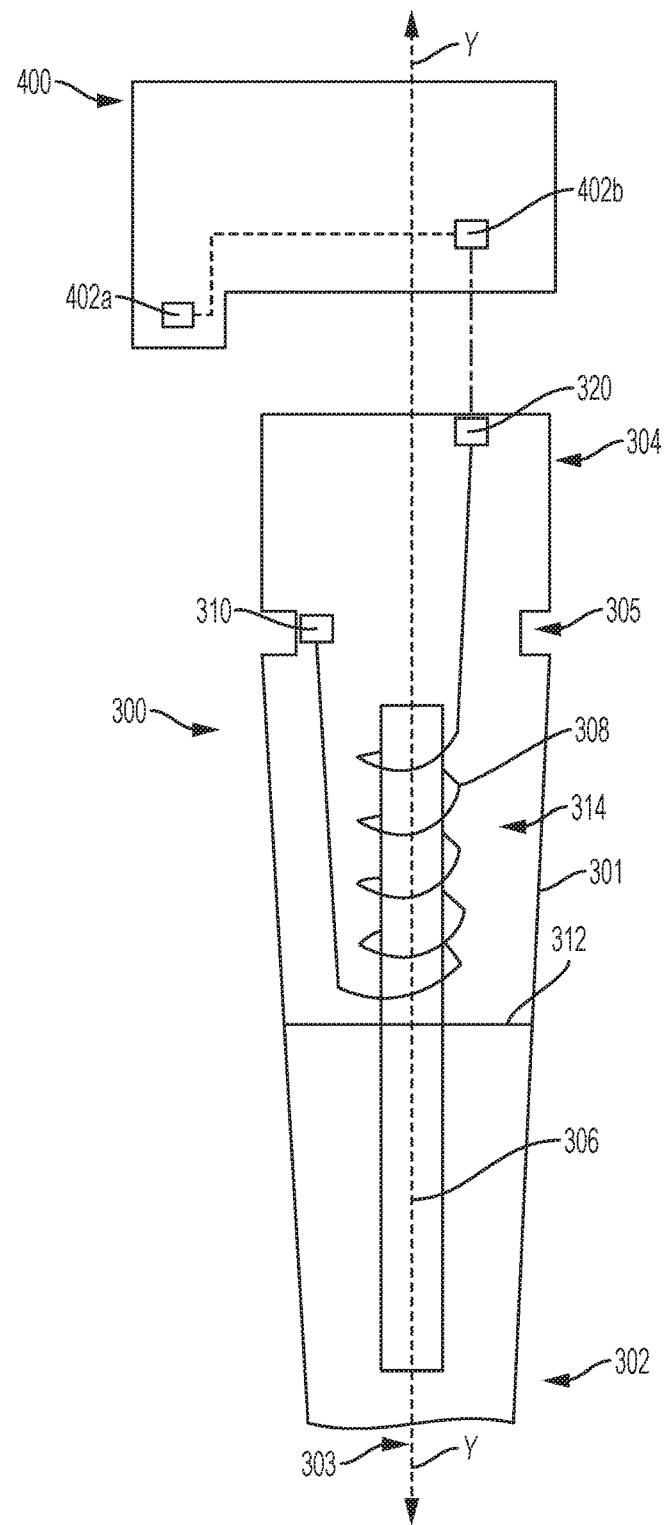
Figure 4B:
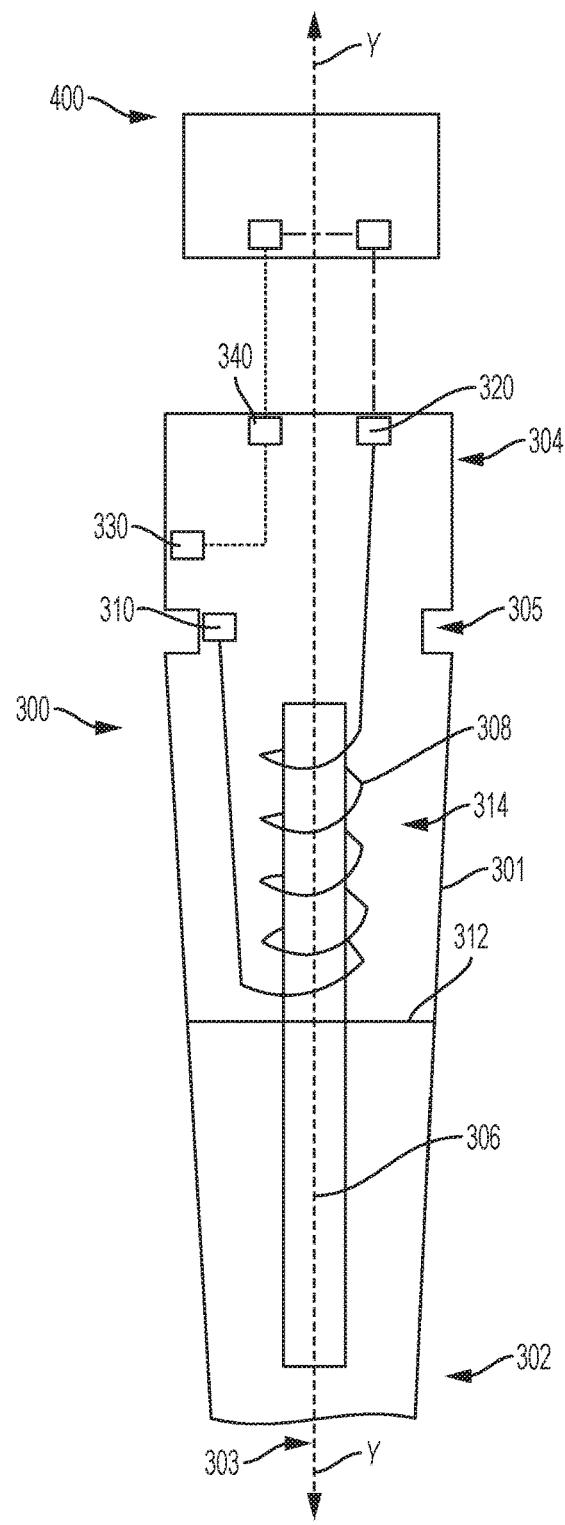
Figure 5A:
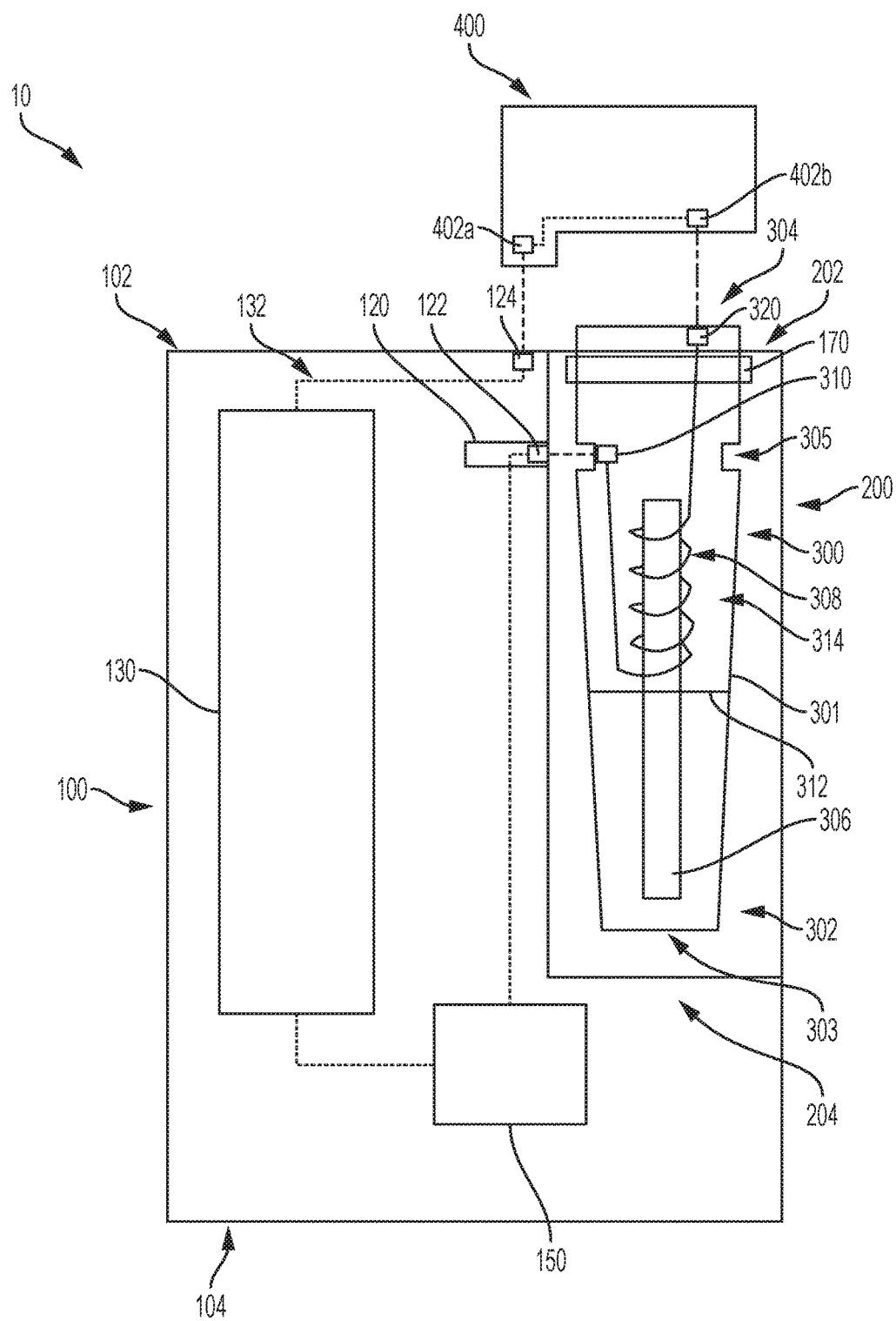
Figure 5B:
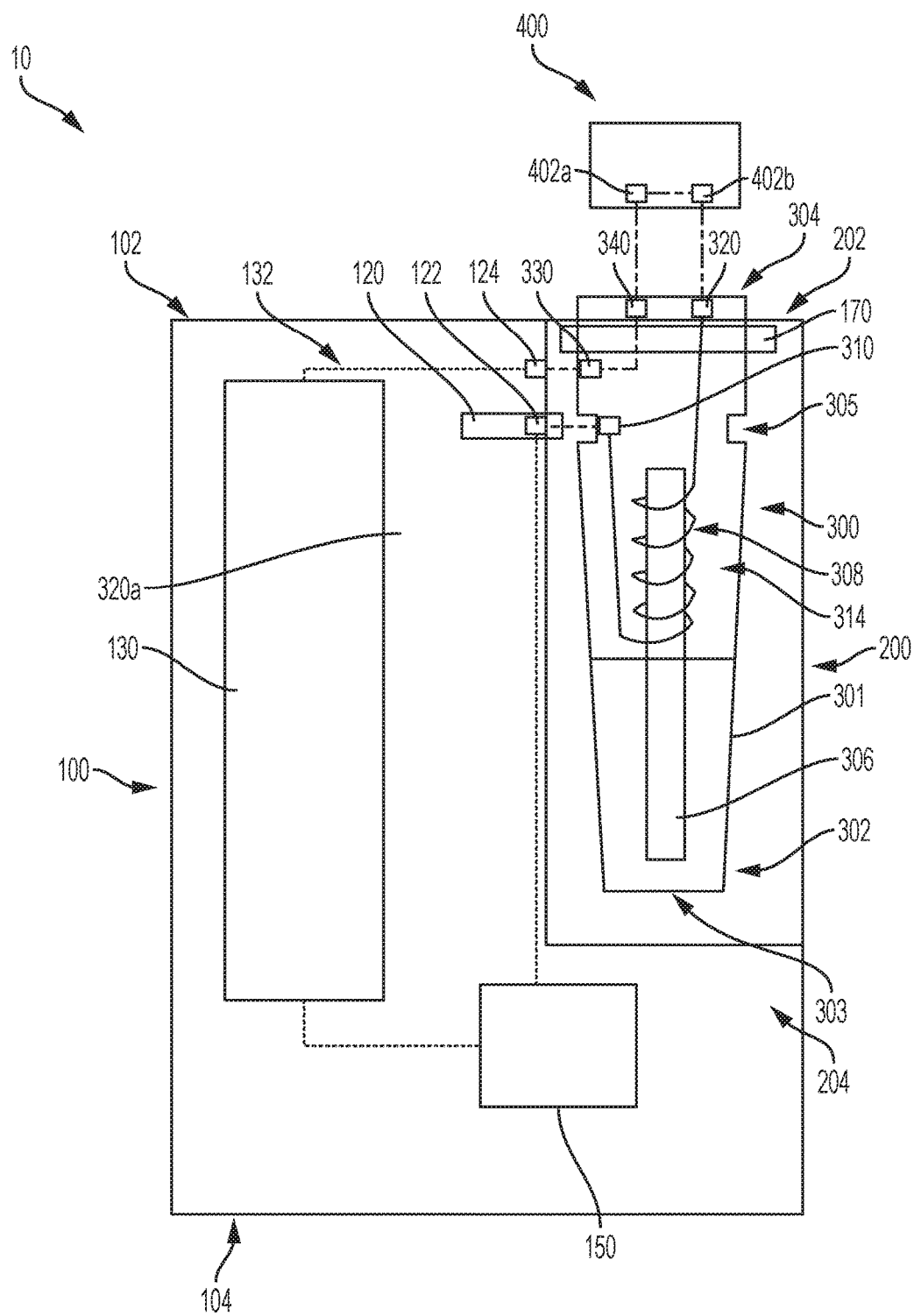
Figure 6:
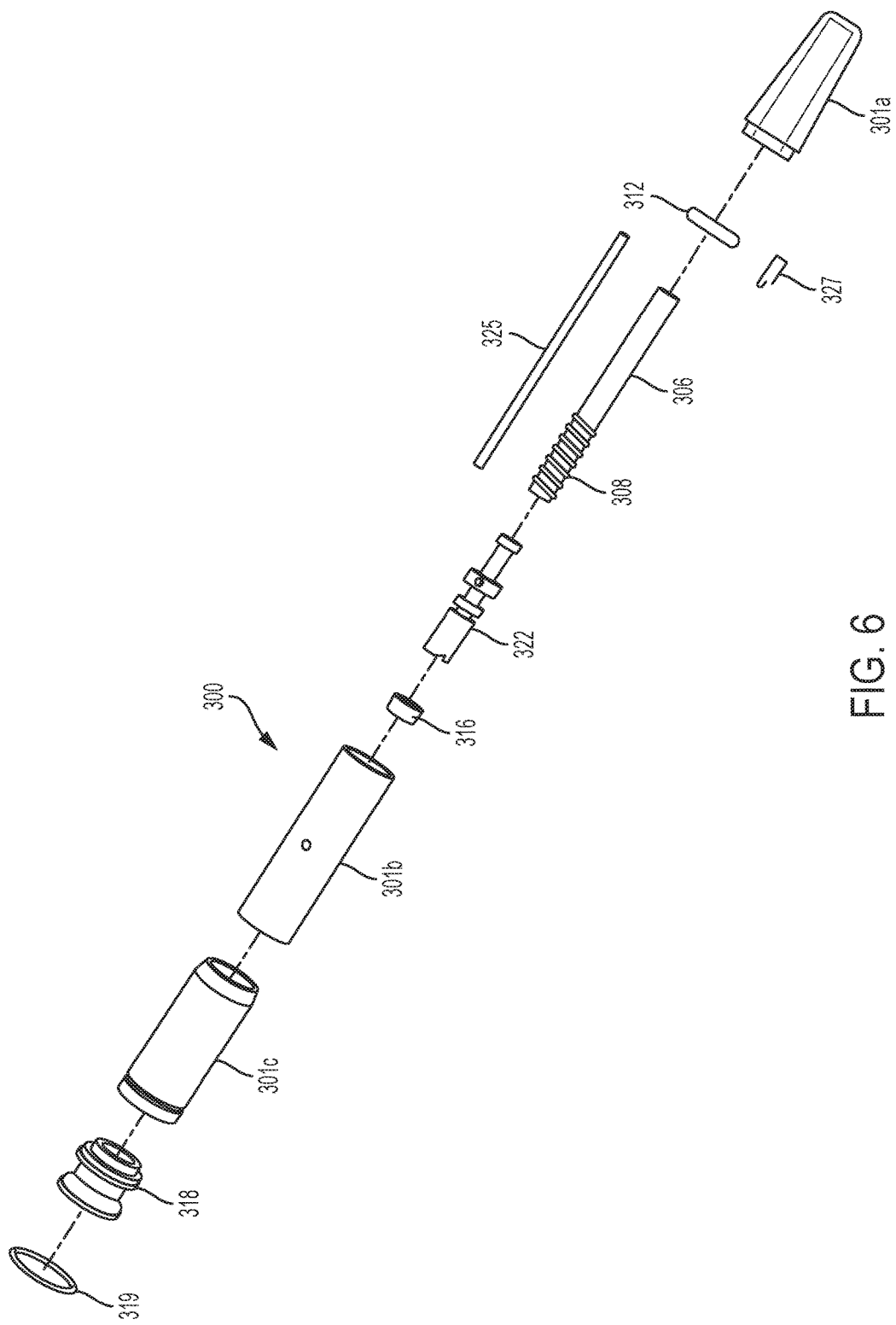
Figure 7A:
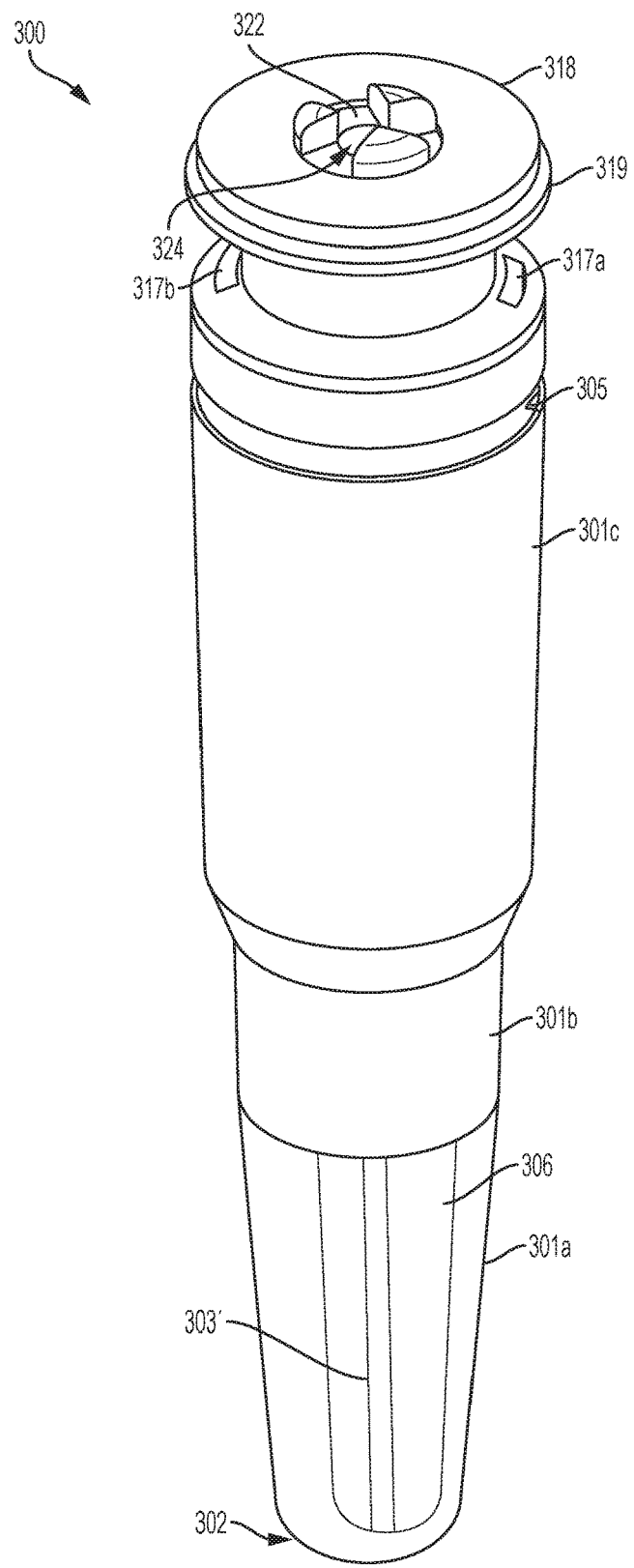
Figure 7B:
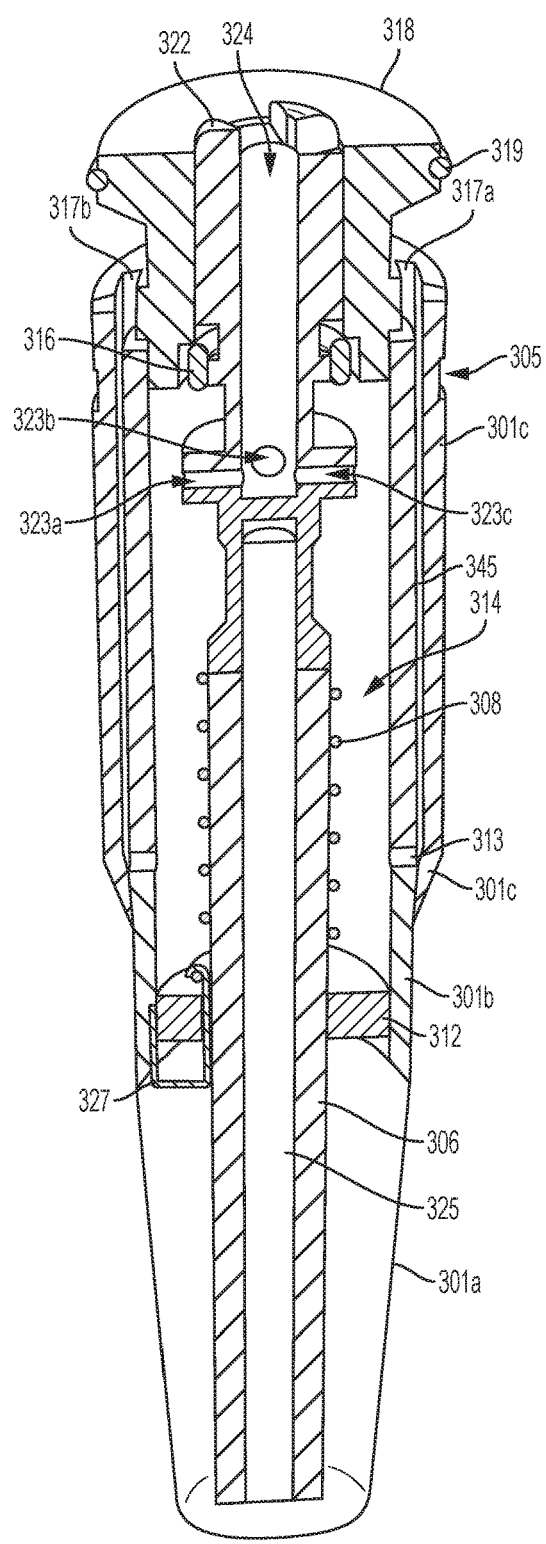
Figure 8:
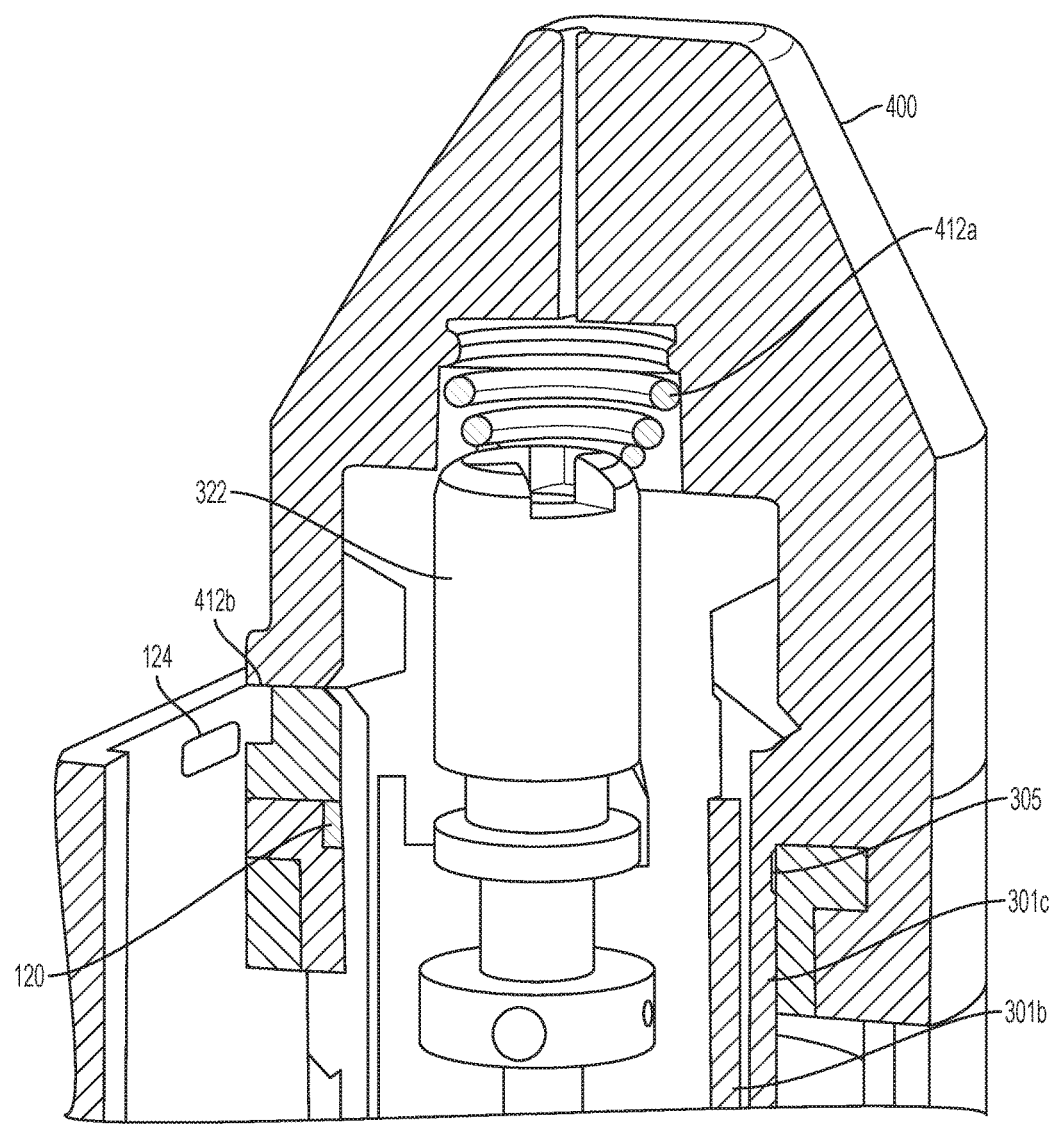
Figure 9:
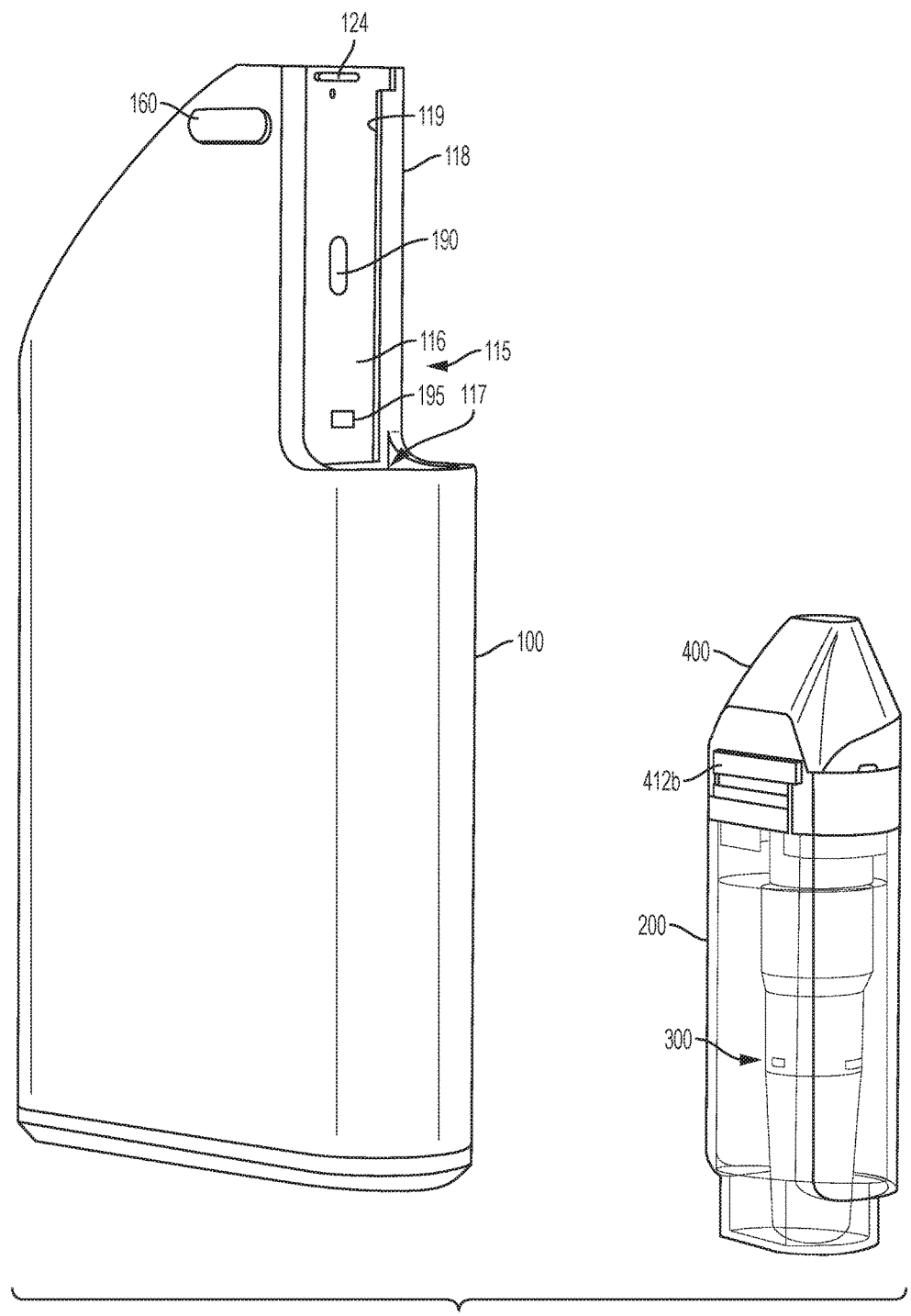
Figure 10:
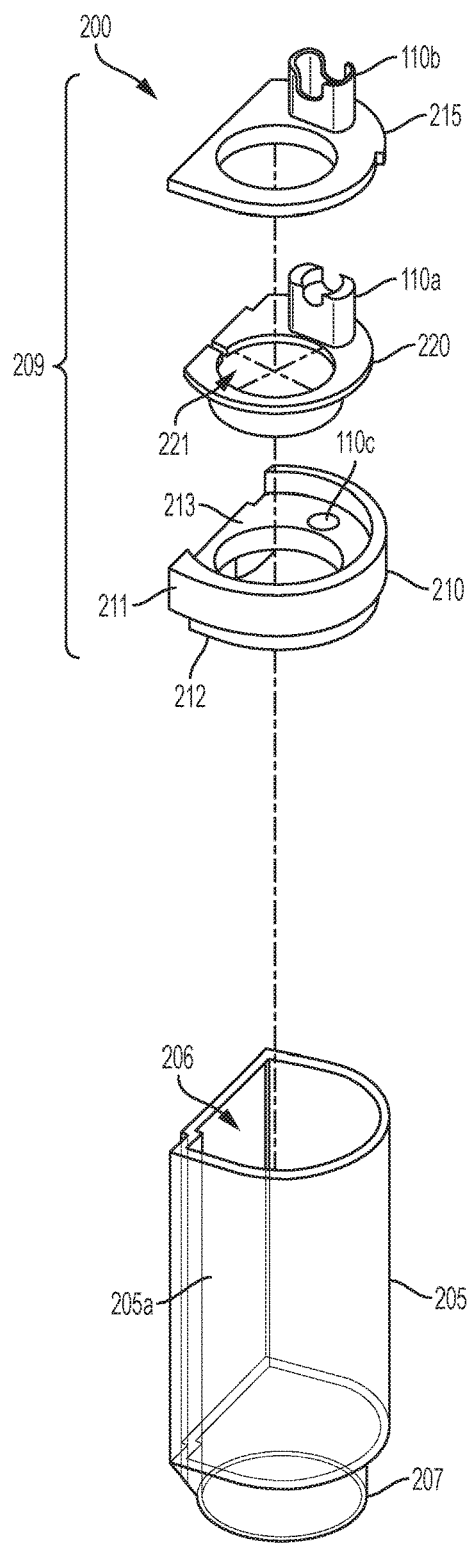
Figure 11:
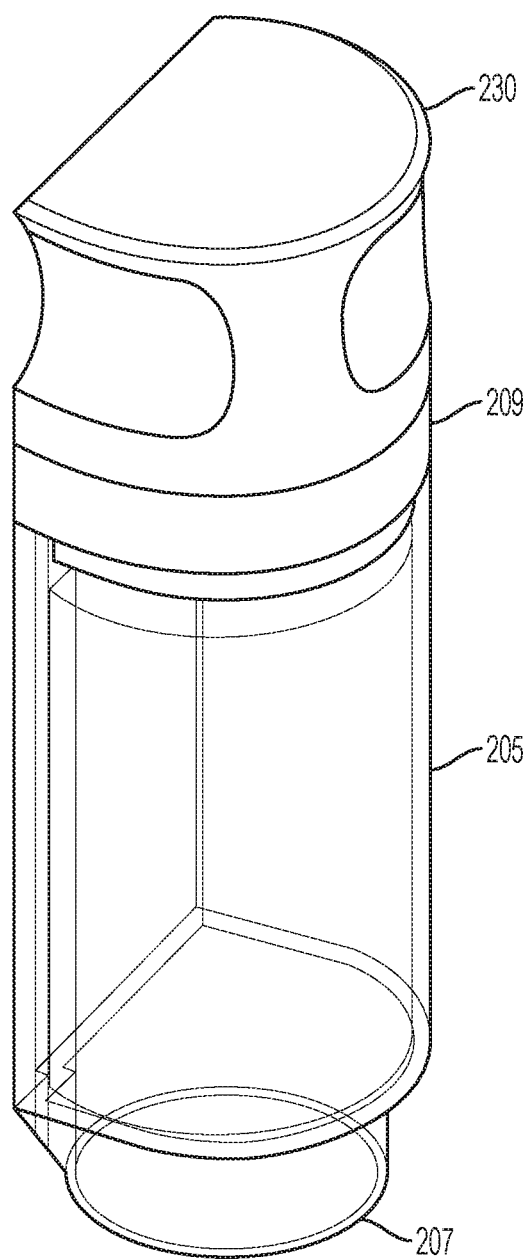
Figure 12:
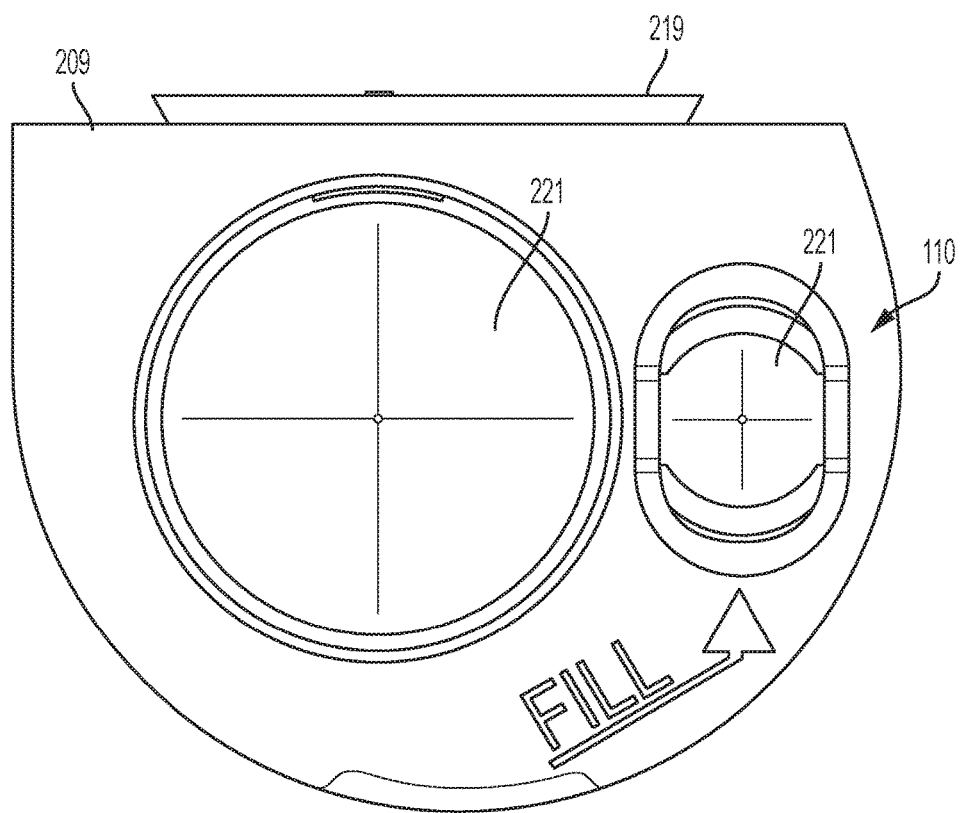

Having thus described the disclosure in the foregoing general terms, reference will now be made to the accompanying drawings, which are not necessarily drawn to scale, and wherein:

FIG. 1 illustrates an aerosol delivery device according to one aspect of the present disclosure;

FIG. 2 illustrates an exploded view of select components of the aerosol delivery device of FIG. 1 according to one aspect of the present disclosure;

FIG. 3A illustrates a top view of an aerosol delivery device according to one aspect of the present disclosure;

FIG. 3B illustrates a top view of an aerosol delivery device according to another aspect of the present disclosure;

FIG. 4A illustrates a schematic diagram of a vaporizing unit of an aerosol delivery device according to one aspect of the present disclosure;

FIG. 4B illustrates a schematic diagram of a vaporizing unit of an aerosol delivery device according to one aspect of the present disclosure;

FIG. 5A illustrates a schematic diagram of an aerosol delivery device that includes the vaporizing unit of FIG. 4A according to one aspect of the present disclosure;

FIG. 5B illustrates a schematic diagram of an aerosol delivery device that includes the vaporizing unit of FIG. 4B according to one aspect of the present disclosure;

FIG. 6 illustrates an exploded view of a vaporizing unit of an aerosol delivery device according to one aspect of the present disclosure;

FIG. 7A illustrates a perspective view of a vaporizing unit of an aerosol delivery device according to one aspect of the present disclosure;

FIG. 7B illustrates a cross-sectional view of a vaporizing unit of an aerosol delivery device according to one aspect of the present disclosure;

FIG. 8 illustrates an exploded view of a reservoir assembly of an aerosol delivery device according to one aspect of the present disclosure;

FIG. 9 illustrates a reservoir assembly of an aerosol delivery device according to one aspect of the present disclosure;

FIG. 10 illustrates an expanded view of a removable reservoir according to one aspect of the present disclosure;

FIG. 11 illustrates a removable reservoir according to one aspect of the present disclosure; and FIG. 12 illustrates a top view of a reservoir according to one aspect of the present disclosure.

DETAILED DESCRIPTION OF THE DISCLOSURE

The present disclosure will now be described more fully hereinafter with reference to exemplary aspects thereof.

These exemplary aspects are described so that this disclosure will be thorough and complete, and will fully convey the scope of the disclosure to those skilled in the art. Indeed, the disclosure may be expressed in many different forms and should not be construed as limited to the aspects set forth herein; rather, these aspects are provided so that this disclosure will satisfy applicable legal requirements. As used in the specification, and in the appended claims, the singular forms "a", "an", "the", include plural referents unless the context clearly dictates otherwise.

As described hereinafter, aspects of the present disclosure are related to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors/aerosols resulting from volatilization or vaporization of certain components such as, for example, an aerosol precursor composition incorporated therein. In preferred aspects, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces and/or components of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article (e.g., a cigarette, cigar or pipe that is employed by lighting with a flame and used by inhaling tobacco that is subsequently burned and/or combusted), draw on one end of that piece for inhalation of aerosol produced by that piece, take or draw puffs at selected intervals of time, and the like. The devices described herein, however, are not limited to devices that are substantially shaped and dimensioned as a traditional cigarette. Rather, the present devices may take on any shape and can be substantially larger than a traditional cigarette. In certain preferred aspects, the device may be sufficiently compact to be considered "hand-held" devices.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

According to aspects of the present disclosure, the aerosol precursor composition can vary. Most preferably, the aerosol precursor composition is comprised of a combination or mixture of various ingredients or components. The selection of the particular aerosol precursor components, and the relative amounts of those components used, may be altered in order to control the overall chemical composition of the mainstream aerosol produced by the aerosol generation arrangement(s). Of particular interest are aerosol precursor compositions that can be characterized as being generally liquid in nature. For example, representative generally liquid aerosol precursor compositions may have the form of liquid solutions, viscous gels, mixtures of miscible components, or liquids incorporating suspended or dispersed components. Typical aerosol precursor compositions are capable of being vaporized upon exposure to heat under those conditions that are experienced during use of the aerosol generation arrangement(s) that are characteristic of the present disclosure; and hence are capable of yielding vapors and aerosols that are capable of being inhaled.

According to some aspects, the aerosol delivery device may include or incorporate tobacco, a tobacco component, or a tobacco-derived material (i.e., a material that is found naturally in tobacco that may be isolated directly from the tobacco or synthetically prepared). For example, the aerosol delivery device may include an amount of flavorful and aromatic tobaccos in cut filler form. In some aspects, the aerosol precursor composition may include tobacco, a tobacco component, or a tobacco-derived material that is processed to provide a desired quality, such as those processed according to methods described in U.S. Pat. No. 9,066,538 to Chen et al.; U.S. Pat. No. 9,155,334 to Moldoveanu et al.; U.S. Pat. App. Pub. No. 2016/0015078 to Moldoveanu et al.; U.S. patent application Ser. No. 15/043,177, filed Feb. 12, 2016 to Marshall et al.; the disclosures of which are incorporated in their entirety herein by reference.

Additionally or alternatively, highly purified tobacco-derived nicotine (e.g., pharmaceutical grade nicotine having a purity of greater than 98% or greater than 99%) or a derivative thereof can be incorporated in the aerosol precursor composition. Representative nicotine-containing extracts can be provided using the techniques set forth in U.S. Pat. No. 5,159,942 to Brinkley et al., which is incorporated herein by reference. In certain embodiments, the products of the invention can include nicotine in any form from any source, whether tobacco-derived or synthetically-derived. Nicotinic compounds used in the products of the invention can include nicotine in free base form, salt form, as a complex, or as a solvate. See, for example, the discussion of nicotine in free base form in U.S. Pat. No. 8,741,348 to Hansson et al., which is incorporated herein in its entirety by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al., which is incorporated herein in its entirety by reference. At least a portion of the nicotine can be employed in the form of a salt. Salts of nicotine can be provided using the types of ingredients and techniques set forth in U.S. Pat. No. 2,033,909 to Cox et al.; U.S. Pat App. Pub. No. 2015/0344456 to Dull et al.; U.S. patent application Ser. No. 15/951,939, filed Nov. 25, 2015 to Dull et al.; and Perfetti, Beitrage Tabakforschung Int., 12, 43-54 (1983), the disclosures of which are incorporated herein in their entirety by reference. Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate), chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid, as discussed in U.S. Pat. Pub. No. 2011/0268809 to Brinkley et al., which is incorporated herein in its entirety by reference.

In another aspect, the aerosol precursor composition may include tobacco, a tobacco component, or a tobacco-derived material that may be treated, manufactured, produced, and/or processed to incorporate an aerosol-forming material (e.g., humectants such as, for example, propylene glycol, glycerin, and/or the like). Additionally or alternatively, the aerosol precursor composition may include at least one flavoring agent. Additional components that may be included in the aerosol precursor composition are described in U.S. Pat. No. 7,726,320 to Robinson et al., which is incorporated herein by reference. Various manners and methods for incorporating tobacco and other ingredients into aerosol generating devices are set forth in U.S. Pat. No. 4,947,874 to Brooks et al.; U.S. Pat. No. 7,290,549 to Banerjee et al; U.S. Pat. No. 7,647,932 to Cantrell et al.; U.S. Pat. No. 8,079,371 to Robinson et al.; and U.S. Pat. App. Pub. Nos. 2007/0215167 to Crooks et al.; 2016/0073695 to Sears et al., the disclosures of which are incorporated herein by reference in their entirety.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. In exemplary embodiments, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one aspect, all of the components of the aerosol delivery device are contained within a single housing. Alternatively, an aerosol delivery device can comprise two or more housings that are joined and are separable.

Aerosol delivery devices of the present disclosure can be formed of an outer housing or shell that is not substantially tubular in shape but may be formed to substantially greater dimensions—i.e., be substantially "palm-sized" for being held in the palm of a user. The housing or shell can be configured to include a mouthpiece and/or may be configured to receive a separate shell (e.g., a cartridge) that can include consumable elements, such as a liquid aerosol precursor composition. In some aspects, the housing or shell can be configured to receive a separate shell that may include a vaporizer or atomizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in the background art section of the present disclosure. One example aspect of an aerosol delivery device 10 according to the present disclosure is provided in FIG. 1. The aerosol delivery device 10 includes a housing 100, a reservoir 200, and a vaporizing unit 300.

In various aspects, the present disclosure is particularly beneficial in that the use of a replaceable vaporizing unit 300 and a reservoir 200 in an aerosol delivery device 10 can provide for ease of filling the reservoir 200 with an aerosol precursor composition. Many conventional aerosol delivery devices (e.g., electronic cigarettes) utilize combinations of components to form an aerosol from the aerosol precursor composition stored within the reservoir. For example, some conventional aerosol delivery devices include a heater or heating element (e.g., an electrical resistance heating element or component commonly referred to as an "atomizer") within the same housing that defines a reservoir. The atomizers incorporated within these conventional aerosol delivery devices typically are not replaceable, and are thus disposed of when a component of the atomizer malfunctions and/or fails. Additionally, some conventional aerosol delivery devices may include replaceable components such as, for example, a heater or heating element and/or a wick, but may include numerous parts that are difficult and/or complicated to operate. For example, some traditional aerosol delivery devices may include a replaceable atomizer disposed within a reservoir body that may require emptying the reservoir of remaining aerosol precursor composition before replacing the atomizer. Further, some conventional aerosol delivery devices may include a reservoir configured to receive a vaporizing unit through one open end and the aerosol precursor composition from an opposing second open end. Such devices suffer from various disadvantages such as, for example, difficulties in assembling and operating (e.g., disassembling the atomizer to fill the reservoir with the aerosol precursor composition, emptying the reservoir of the aerosol precursor composition to replace a heating element and/or liquid transport element, etc.) the aerosol delivery device by a user.

An aerosol delivery device 10 according to aspects of the present disclosure can provide ease of use during operation (e.g., refilling the reservoir with an aerosol precursor composition, replacing a heating element and/or liquid transport element, etc.). For example, the ability to replace the vaporizing unit 300 without having to empty the reservoir 200 of the aerosol precursor composition can provide for an improved user experience.

As shown in FIGS. 1, 2, 3A and 3B, the housing 100 includes a top surface 102 and a bottom surface 104. The top surface 102 defines at least one orifice (e.g., a vaporizing orifice 108). In some aspects, the top surface 102 of the housing 100 defines both a vaporizing orifice 108 and a fill orifice 110. The vaporizing orifice 108 may be in fluid communication with the reservoir 200. For example, the reservoir 200 includes an open end 202 and an opposing closed end 204. The open end 202 of the reservoir 200 may be in fluid communication with the vaporizing orifice 108. Additionally, the open end 202 of the reservoir 200 may be in fluid communication with the fill orifice 110. As such, it is understood that the open end 202 of the reservoir 200 is considered "open" in that a vaporizing unit 300 may be removably inserted into the open end 202 of the reservoir 200.

Referring to FIG. 1, the reservoir 200 may be disposed within the housing 100 or attached to the housing 100. That is, in some aspects, the reservoir 200 may be integrally formed within the housing 100 and may be configured to be securely retained therein, or the reservoir 200 may be integrally secured to the housing 100 such that at least a portion of the reservoir 200 forms at least a portion of an outer surface of the aerosol delivery device 10. Alternatively, the reservoir 200 may be configured to be removably engaged with the housing 100 (e.g., being removably insertable within the housing or being removably attachable with the housing). Although illustrated as being substantially cylindrical in shape, the reservoir 200 may be any suitable shape that includes an open end 202 and an opposing closed end 204. In some aspects, the reservoir 200 may be shaped so as to retain a desired amount of the aerosol precursor composition therein. For example, the reservoir 200 may be configured to retain an aerosol precursor composition therein, and the reservoir 200 may be formed of a material that is impermeable to the aerosol precursor composition. In some aspects, the reservoir 200 can be formed of a metallic material, a ceramic material, a glass material, a polymeric material, or combinations thereof. The reservoir 200 may be shaped so as to retain a limited amount of aerosol precursor composition therein to provide for many of the sensations (e.g., inhalation and exhalation rituals, types of tastes or flavors, organoleptic effects, etc.) of smoking a particular amount of traditional types of smoking articles (e.g., cigarettes, cigars, pipes, etc.).

Embodiments incorporating a removable reservoir 200 are particularly illustrated in reference to FIG. 9, FIG. 10, and FIG. 11. A removable reservoir 200 can be defined by an outer wall 205 with an open top 206 and a closed bottom 207. A lower portion of the reservoir wall 205 can be inset and have reduced dimensions relative to the remaining portion of the reservoir wall 205. A cover 209 for the reservoir 200 can be formed of a lower gasket housing 210, an upper gasket housing 215, and an intervening gasket 220, which includes a resealing membrane 221 through which a vaporizing unit 300 can be inserted. The lower gasket housing 210 includes a bottom inset wall 212 that engages the open top 206 of the outer wall 205 of the reservoir 200 and includes a top rim wall 211 that sits atop the wall 205 of the reservoir 200. The intervening gasket 220 is positioned on the base 213 of the lower gasket housing 210, and the upper gasket housing 215 is positioned thereon such that the upper gasket housing 2105 and the lower gasket housing 210 are interconnected. When properly aligned, the gasket extension 110*a*, the upper gasket housing extension surround 110*b*, and the lower gasket housing gasket port 110*c* are aligned to form the fill orifice 110. A reservoir cap 230 can be attached to the top of the reservoir during storage.

The housing 100 can include a cut-out 115 configured to receive the removable reservoir 200, and the cut-out 115 can define a cut-out wall 116 and a cut-out floor 117, which can be recessed relative to a cut-out rim 118. The reservoir 200 can be aligned in the cut-out 115 so that a back face 205*a* of the reservoir wall 205 is positioned against the cut-out wall 116, and the closed bottom 207 of the reservoir wall 207 is positioned against the cut-out floor 117. The cut-out rim 118 can be configured to secure the reservoir 200 in place when aligned in the cut-out 115. The cut-out rim 118, for example, may include a groove 119 that can align with a tongue 219 formed on the wall 205 of the reservoir 200 (see FIG. 12). If desired, a locking mechanism can be included to further secure the reservoir 200 in the cut-out 115 of the housing 100. The back face 205*a* of the reservoir wall 205 can be textured, include a surface treatment, or incorporate other elements useful to configure the back face 205*a* for improved transmittance and/or diffusion of light from the LED 190 positioned on the cut-out wall 116 of the housing 100. In this manner, the reservoir housing 200 can define a light pipe. In some embodiments, a sensor 195 may also be present on the cut-out wall 116 and/or the cut-out floor 117. The sensor 195 can be configured to detect a properly inserted reservoir 200, read a corresponding signal on the reservoir 200 to confirm that a genuine and compatible reservoir is being used, detect the level of the aerosol precursor composition in the reservoir 200, and the like.

Referring to FIG. 2, the aerosol delivery device 10 further includes a vaporizing unit 300 configured to removably engage the open end 202 of the reservoir 200. The vaporizing unit 300 includes a liquid transport element 306 and a heating element 308 (shown in FIG. 4A and FIG. 4B) and may include an outer shell 301. In some aspects, the liquid transport element 306 and the heating element 308 are disposed within the outer shell 301. The outer shell 301 may include a first end 302 and an opposing second end 304. Additionally, the outer shell 301 may define an aperture 303 proximate the first end 302 of the outer shell 301. As shown in FIG. 2, the vaporizing unit 300 may include a serially arranged first and second portion that extends between the first end 302 and the opposing second end 304. In some aspects, the first portion may taper towards the first end 302 and the second portion may be substantially cylindrical in shape. In some aspects, the first and second portions may be separated by a gasket 312 or similar element. The out shell 301 thus may, in some embodiments, be formed of a single housing or a plurality of interconnected sub-housings. As illustrated in FIG. 2, first sub-housing 301*a* may interconnect with second sub-housing 301*b* to collectively form the outer shell 301. Moreover, a further outer sub-housing 301*c* may be included. As further discussed herein, such third sub-housing 301*c* can function to direct air intake to the vaporizer 300. The vaporizing unit 300 is configured to removably engage the open end 202 of the reservoir 200 by extending therethrough. For example, the open end 202 of the reservoir 200 may define an orifice configured to receive the vaporizing unit 300 therethrough. That is, removably engaging the vaporizing unit 300 with the reservoir 200 may include inserting the first end 302 of the vaporizing unit 300, and thus the aperture 303 disposed proximate the first end 302, through the orifice defined by the open end 202 of the reservoir. In some aspects, the reservoir orifice configured to receive the vaporizing unit 300 may be shaped and/or sized to sealably engage the vaporizing unit 300 (i.e., the diameter of the reservoir orifice may be substantially similar to the greatest diameter of the vaporizing unit 300). Referring to FIGS. 5A and 5B, when the vaporizing unit 300 is removably engaged with the open end 202 of the reservoir 200, the aperture 303 defined proximate the first end 302 of the outer shell 301 may be in fluid communication with the reservoir 200. Further, the liquid transport element 306 may be arranged within the outer shell 301 so as to be in fluid communication with the aperture 303 such that when the vaporizing unit 300 is removably engaged with the open end 202 of the reservoir 200, the liquid transport element 306 may be in fluid communication with the reservoir 200 and may be arranged with respect to the reservoir 200 to transfer the aerosol precursor composition from the reservoir 200 to the heating element 308. That is, when the vaporizing unit 300 is disposed in the operating position, the liquid transport element 306 may be in fluid communication with the reservoir 200 so as to transfer a desired amount of the aerosol precursor composition from the reservoir 200 to the heating element 308. In some aspects, the liquid transport element 306 may be arranged parallel to the longitudinal axis Y of the vaporizing unit outer shell 301, as shown in FIGS. 4A and 4B.

The liquid transport element 306 may include materials configured to facilitate the transfer of the aerosol precursor composition from the reservoir 200 to the heating element 308. That is, the liquid transport element 306 can be absorbent, adsorbent, or otherwise adapted to retain the aerosol precursor composition. As such, the aerosol precursor composition can be characterized as being coated on, adsorbed by, or absorbed by the porous media. According to some aspects, the liquid transport element 306 may include a flexible material such as, for example, fibers and/or fibrous materials (e.g., woven or non-woven fabrics). Additionally or alternatively, the liquid transport element 306 may include a braided material, such as those described in U.S. Pat. No. 8,910,640 to Sears et al. Non-limiting examples may further include natural and synthetic fibers, such as cotton, cellulose, polyesters, polyamides, polylactic acids, glass fibers, combinations thereof, and the like. According to some aspects, the liquid transport element 306 may include a non-flexible material such as, for example, metals, ceramics and/or the like. Other exemplary materials that can be used in the liquid transport element 306 to transport the aerosol precursor composition from the reservoir 200 to the heating element 308 may include carbonized filaments (e.g., a material formed of a carbonaceous material that has undergone calcining to drive off non-carbon components of the material), and foams, such as carbon foams. Examples of suitable materials for use as a liquid transport element are described in U.S. Pat. Pub. No. 2015/0059780 to Davis et al.; U.S. Pat. Pub. No. 2014/0261487 to Chapman et al.; U.S. Pat. Pub. No. 2013/0255702; and U.S. application Ser. No. 14/988,109, filed Jan. 5, 2016, the disclosures of which are incorporated herein by reference.

Referring to FIGS. 4A and 4B, the vaporizing unit 300 may further include a gasket 312 configured to substantially seal portions of the vaporizing unit 300 from the aerosol precursor composition when the vaporizing unit 300 is removably engaged with the open end 202 of the reservoir 200 and/or disposed in the operating position. That is, the gasket 312 may be configured to substantially seal portions of the vaporizing unit 300 and substantially prevent excess amount of aerosol precursor composition from entering the sealed portion (e.g., a vapor forming chamber 314) when the vaporizing unit 300 is in fluid communication with the reservoir 200. Additionally, the gasket 312 may define a liquid transport element aperture configured to receive the liquid transport element 306 therethrough such that the liquid transport element 306 may transport the aerosol precursor composition from the reservoir 200 to the heating element 308, which may be disposed within the vapor forming chamber 314 of the vaporizing unit 300.

As shown in FIGS. 2, 4A and 4B, the outer shell 301 may further define an annular channel 305 proximate the opposing second end 304 of the outer shell 301 of the vaporizing unit 300. Referring to FIGS. 5A and 5B, the aerosol delivery device 10 may include an engaging element 120 configured to operably engage the vaporizing unit 300 when the vaporizing unit 300 is engaged with the reservoir 200 and/or disposed in the operating position. For example, the engaging element 120 may be configured to operably engage the annular channel 305 when the vaporizing unit 300 is disposed in the operating position. As shown in FIGS. 4A-5B, the vaporizing unit 300 may include at least one electrical connector 310. In some aspects, as shown in FIGS. 4B and 5B, the vaporizing unit 300 may include a first electrical connector 310a and a second electrical connector 310b configured to engage respective first and second electrical contacts 122a, 122b disposed in or on the housing 100.

According to some aspects, as shown in FIGS. 4A and 5A, the annular channel 305 may include the electrical connector 310 configured to engage the electrical contact 122 disposed in or on the housing 100 of the aerosol delivery device 10. In some aspects, the electrical connector 310 may be configured to coupleably engage the engaging element 120, which may include the electrical contact 122, when the vaporizing unit 300 is disposed in the operating position. For example, the engaging element 120 may include a biasing element configured to bias the electrical contact 122 towards the electrical connector 310 in the annular channel 305 such that when the vaporizing unit 300 is disposed in the operating position, the biasing element causes the electrical contact 122 to engage the electrical connector 310 of the vaporizing unit 300. According to some aspects, the engaging element may include a channel within the housing configured to coupleably engage a reciprocally shaped member of the vaporizing unit that includes the electrical connector.

The heating element 308 may be in in a heating arrangement with the liquid transport element 306. In particular, the heating element 308 may extend at least partially about a portion of the liquid transport element 306, and more particularly, may extend at least partially about the liquid transport element 306 at a position between the first end and an opposing second end of the liquid transport element 306. In some aspects, the heating element 308 may be configured to heat the aerosol precursor composition coated on, adsorbed by, or absorbed by the portion of the liquid transport element 306 proximate the heating element 308 to produce an aerosol for inhalation by a user. In particular, the heating element 308 may be formed from a material that provides resistive heating when an electrical current is applied thereto. According to some aspects, the heating element 308 may include a carbon heater. As previously mentioned, the liquid transport element 306 may include a carbon wick, and the outer shell 301 of the vaporizing unit 300 may include a carbon material. Such materials may advantageously provide for environmentally friendly disposal of the vaporizing unit 300.

Referring to FIGS. 4A and 4B, the heating element 308 may include a wire defining a plurality of coils wound about a portion of the liquid transport element 306. The heating element 308 may include a wire material that provides resistive heating and may extend between a first electrical terminal (i.e., the electrical connector 310) and a second electrical terminal 320. For example, the wire material may include Kanthal (FeCrAL), Nichrome, Molybdenum disilicide ($MoSi_2$), Molybdenum disilicide doped with Aluminum ($Mo(Si,Al)_2$), ceramics (e.g. a positive temperature coefficient ceramic), titanium, gold, silver, and/or related alloys in some aspects, although various other materials may be employed in other aspects. According to some aspects, the heating element 308 may be formed by winding the wire about the liquid transport element 306 as described in U.S. Pat. No. 9,210,738 to Ward et al., which is incorporated herein by reference in its entirety. However, various other aspects of methods may be employed to form the heating element 308. For example, the heating element 308 may be configured to heat the aerosol precursor composition disposed within the liquid transport element 306 via radiant heating, as described in U.S. patent application Ser. No. 14/808,405, filed Jul. 24, 2015; Ser. No. 14/958,651, filed Dec. 3, 2015, the contents of which are incorporated herein in their entirety by reference. According to some aspects, the heating element 308 may be configured to heat the aerosol precursor composition via inductive heating, such as described in U.S. patent application Ser. No. 14/934,763, filed Nov. 6, 2015, and Ser. No. 15/002,056, filed Jan. 20, 2016, the disclosures of which are incorporated herein by reference. Additionally or alternatively, the heating element 308 may be configured to heat the aerosol precursor composition absorbed by the liquid transport element 306 via conductive heating. In some embodiments, microheaters can be used, such as described in U.S. Pat. No. 8,881,737 to Collett et al.; U.S. Pub. No. 2015/0117841 to Brammer et al.; U.S. Pub. No. 2015/0117842 to Brammer et al.; and U.S. Pub. No. 2015/0114409 to Brammer et al., the disclosures of which are incorporated herein by reference.

According to some aspects, the housing 100, vaporizing unit 300, and the mouthpiece 400 may collectively form an electrical circuit 132. For example, as shown in FIGS. 5A and 5B, when the vaporizing unit 300 is removably engaged with the open end 202 of the reservoir 200, which is included in the housing 100, and is disposed in the operating position, an electrical connector (e.g., the first electrical terminal 310) may engage the electrical contact 122 in or on the housing 100. The electrical contact 122 may be in electrical connection with and/or included in the electrical circuit 132.

In some aspects, the vaporizing unit 300 may include a second electrical terminal 320. The first and second electrical terminals 310, 320 may be configured to provide the heating element 308 with an electrical current when the vaporizing unit 300, the housing 100, and the mouthpiece 400 collectively form the electrical circuit 132. For example, a power source 130 disposed within the housing 100 is configured to provide an electrical current to the heating element 308 (e.g., a resistive heating element) through the completed electrical circuit 132, which includes the first and second electrical terminals 310, 320 of the vaporizing unit 300. In some aspects, as shown in FIGS. 4B and 5B, the vaporizing unit 300 may include a third and fourth electrical terminal 330, 340. The third electrical terminal 330 may be in electrical connection with the fourth electrical terminal 340.

Referring to FIG. 5A, the electrical circuit 132 may be formed when the vaporizing unit 300 engages the open end 202 of the reservoir 200 and the mouthpiece 400 coupleably engages the vaporizing unit 300 and the housing 100 concurrently. Alternatively, as shown in FIG. 5B, the electrical circuit 132 may be formed when the vaporizing unit 300 engages the open end 202 of the reservoir 200 and the mouthpiece 400 coupleably engages only the vaporizing unit 300. That is, the first and second electrical terminals 310, 320 may be configured to provide the heating element 308 with an electrical current when a mouthpiece 400 is coupleably engaged with the vaporizing unit 300 and/or coupleably engaged with the vaporizing unit 300 and the housing concurrently 100.

In some aspects, the mouthpiece 400 may include a first electrical terminal 402a and a second electrical terminal 402b, which are in electrical connection with one another and are each configured to engage a respective electrical terminal (e.g., the second electrical terminal 320 of the vaporizing unit 300, an electrical contact 122 disposed in or on the housing 10, etc.). For example, when the mouthpiece 400 is coupleably engaged with the vaporizing unit 300 and the housing 100 concurrently as shown in FIG. 5A, the first electrical terminal 402a may be engaged and in electrical connection with the second electrical contact 124 disposed in or on the housing 100 to form the electrical circuit 132. Additionally, the second electrical terminal 402b of the mouthpiece 400 may be engaged and in electrical connection with the corresponding second electrical terminal 320 of the vaporizing unit 300 to form the electrical circuit 132. As such, the mouthpiece 400 engaging the housing 100 and the vaporizing unit 300 concurrently when the vaporizing unit 300 is engaged with the housing 100 may form the electrical circuit 132 configured to transmit an electrical current from the power source 130 in the housing 100 to the heating element 308.

According to another aspect, the mouthpiece 400 may be configured to solely engage the vaporizing unit 300 when the vaporizing unit 300 is engaged with the housing 100 so as to form the electrical circuit 132. As shown in FIG. 5B, the first electrical terminal 402a of the mouthpiece 400 may be in electrical connection with the fourth electrical terminal 340 of the vaporizing unit 300 and the second electrical terminal 402b of the mouthpiece 400 may be in electrical connection with the second electrical terminal 320 of the vaporizing unit 300 when the mouthpiece 400 is coupleably engaged with the vaporizing unit 300. Additionally, when the vaporizing unit 300 is removably engaged with the open end 202 of the reservoir 200 and is disposed in the operating position, the third electrical terminal 330 of the vaporizing unit may be configured to engage and be electrically connected with the second electrical contact 124 disposed in or on the housing 100 so as to form the electrical circuit 132. That is, as shown in FIGS. 5A and 5B, when the electrical circuit 132 is collectively formed by the housing 100, the vaporizing unit 300 and the mouthpiece 400, the power source 130 disposed within the housing 100 may provide an electrical current to the heating element 308 through the completed electrical circuit 132.

An exploded view of an exemplary embodiment of a vaporizing unit 300 according to the present disclosure is shown in FIG. 6. It is understood that such embodiment is only one example of a vaporizing unit 300 suitable for use according to the present disclosure, and the devices 10 discussed herein are not limited to only this single embodiment. As illustrated, the vaporizing unit 300 comprises: a first sub-housing 301a; a gasket 312; an outer coil contact 327; a central coil contact 325; a liquid transport element 306; a heating element 308; a flow tube 322; a flow tube gasket 316; a second sub-housing 301b; a third sub-housing 301c; a vaporizing unit cap 318; and an O-ring 319.

The structure of the vaporizing unit 300 according to this embodiment is further illustrated in FIG. 7A and FIG. 7B. In particular, the first sub-housing 301*a* is sealed at its end 302 but includes an aperture 303 or a plurality of apertures formed in the wall of the first sub-housing 301*a* such that the first sub-housing 301*a* can function as a capillary tube surrounding a portion of the liquid transport element 306 to meter the aerosol precursor composition from the reservoir 200. The first sub-housing 301*a* interconnects with the second sub-housing 301*b* proximate the gasket 312 that is effective to separate the vapor forming chamber 314 from the aerosol precursor composition intake within the first sub-housing 301*a*. The third sub-housing 301*c* is sheathed around at least a portion of the second sub-housing 301*b*, and a space between the inner surface of the third sub-housing 301*c* and the outer surface of the second sub-housing 301*b* defines an air intake channel 345. The air intake channel 345 may comprise an annular space completely encircling the second sub-housing 301*b* or may comprise one or more individual channels. One or more vapor forming chamber air inlets 313 are formed in the second sub-housing 301*b* to direct air passing through the air intake channel 345 into the vapor forming chamber 314. Inside the vapor forming chamber 314, the heater 308 is coiled around the liquid transport element 306. The liquid transport element 306 is adjacent an end of the flow tube 322, which flow tube includes aerosol exit ports 323*a*, 323*b*, and 323*c* (although the exact number of aerosol exit ports can vary with the condition of at least on aerosol exit port being present in the flow tube 322). The aerosol exit ports 323*a*, 323*b*, and 323*c* open into the aerosol exit channel 324, which is open at the end engaging the vaporizing unit cap 318. The flow tube 322 specifically passes through a channel through the vaporizing unit cap 318. The flow tube gasket 316 surrounds the flow tube 322 and prevents passage of air or vapor between the flow tube 322 and the vaporizing unit cap 318. The vaporizing unit cap 318 includes air intake ports 317*a* and 317*b*, which are in fluid communication with the air intake channel 345. The O-ring 319 forms a seal with the interior of the mouthpiece 400.

In use, with further reference to FIG. 7A and FIG. 7B, aerosol precursor composition travels through the liquid transport element 306 into the vapor forming chamber 314 where it is vaporized by the heater 308. When a user draws on the mouthpiece 400 (see FIG. 1 and FIG. 2), which is in fluid communication with the open end 304 of the vaporizing unit 300, air enters the air intake ports 317*a* and 317*b*, passes through the air intake channel 345, and through the vapor forming chamber air inlets 313 to mix with the formed vapor in the vapor forming chamber 314. The air mixing with the vapor forms and aerosol that is drawn through the aerosol exit ports 323*a*, 323*b*, and 323*c* and into the aerosol exit channel 324 where it passes through the mouthpiece 400.

With reference to FIG. 8, the aerosol delivery device 10 provides safe electrical connections to prevent activation of the heater 308 in the atomizing unit 300 unless the device is fully assembled with the mouthpiece 400 in place. More particularly, referring to FIG. 5A, FIG. 7B, and FIG. 8, when the atomizing unit 300 is fully inserted into the reservoir 200, the engaging element 120 (e.g., a spring-loaded detent) engages the annular channel 305 to form an electrical connection to the outer coil contact 327 via the second sub-housing 301*b* and the third sub-housing 301*c*. The outer coil contact 327 connects to one end of the heater 308, and the second end of the heater 308 connects to the central coil contact 325, which makes an electrical connection with the flow tube 322. When the mouthpiece 400 is placed on the device 10, an electrical contact spring 412*a* makes an electrical connection with the flow tube 322, and a mouthpiece contact 412*b* makes an electrical connection with the electrical contact 124 on the housing. The electrical contact 124 and the engaging element 120 are in electrical connection with the battery 130, thus completing the circuit. In this manner, removal of the mouthpiece breaks the electrical connection preventing accidental heating of the vaporizing unit 300 during removal and replacement.

The mouthpiece 400 also can include on or more air openings 417 for in-flow of air as discussed above. The air openings 417 can be adjustable to control the amount of air entering the device 10.

According to some aspects, the power source 130 may include a battery disposed within the housing 100. In some aspects, a power source within the housing 100 may be referred to as being disposable or as being reusable. For example, the power source may include a replaceable power source such as replaceable battery. In another aspect, the power source may include a rechargeable battery, and thus may be combined with any type of recharging technology, including connection to a typical electrical outlet, connection to a car charger (e.g., a cigarette lighter receptacle), and/or connection to a computer, such as through a universal serial bus (USB) cable. For example, an adaptor including a USB connector at one end and a control body connector at an opposing end is disclosed in U.S. Pat. App. Pub. No. 2014/0261495 to Novak et al., which is incorporated herein by reference in its entirety. Examples of useful rechargeable power sources include lithium ion batteries, and more particularly, lithium polymer batteries. Additional examples of batteries that can be used according to the disclosure are described in U.S. Pat. App. Pub. No. 2010/0028766 to Peckerar et al., the disclosure of which is incorporated herein by reference in its entirety.

In some aspects, the aerosol delivery device 10 may include a plurality of power sources within the housing 100. For example, the aerosol delivery device 10 may include two batteries having different electric charges. According to one aspect, the aerosol delivery device may include a first battery having an electric charge that is approximately half of the electric charge of a second battery within the housing 100. One advantage of incorporating two separate batteries having two different electric charges within the aerosol delivery device 10 is to maximize energy density of the aerosol delivery device 10 and/or to provide more efficient power management while operating the aerosol delivery device 10. Examples of batteries that can be used according to the disclosure are described in U.S. Pat. App. Pub. No. 2010/0028766 to Peckerar et al., the disclosure of which is incorporated herein by reference in its entirety.

The aerosol delivery device 10 may further include indicia and/or other indicators (e.g., light emitting diodes (LED)), which can be variably arranged within and/or on the housing 100, so as to provide an output to the user. Further indicators (e.g., a haptic feedback component, an audio feedback component, an LCD screen, or the like) can be included in addition to or as an alternative to a LED indicator. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. Pat. App. Pub. No. 2015/0216233, to Sears et al.; which are incorporated herein by reference. In some embodiments, for example, an LED 190 can be present on the housing 100. In particular, an LED may be positioned on the housing 100 behind the reservoir 200. Such positioning can be useful for illumination of the reservoir 200 for aesthetics and/or to improve the ability to visualize the amount of aerosol precursor composition remaining in the reservoir 200. The control component 150 can be configured to illuminate the LED under defined conditions for a defined time. For example, when the mouthpiece 400 is removed and the user is refilling the reservoir 200, the device 10 can be configured so that engaging the push-button switch 160 can cause the LED to illuminate the reservoir 200 to improve ease of filling, particularly in low light conditions.

In one aspect, the aerosol delivery device 10 may include a display unit 140 configured to display information concerning the operational status of the aerosol delivery device. For example, as shown in FIGS. 3A and 3B, the display unit 140 may be configured to display an indicia corresponding to the aerosol delivery device settings. For example, as illustrated in the noted figures, the display unit 140 is configured to provide visual indicators in the form of heating element temperature setting indicia 142, power level indicia 144, and operability indicia 146 (e.g., temperature unlocked for use in FIG. 3A and temperature locked in FIG. 3B.

Referring to FIGS. 5A and 5B, the aerosol delivery device 10 may further include a control component 150 (e.g., a microcontroller) and/or an actuating component (e.g., a push-button switch 160) within and/or on the housing 100. For example, as shown in FIGS. 1, 3A, and 3B, the aerosol delivery device 10 may include a membrane potentiometer 162 configured to control functions of the device. In another aspect, the aerosol delivery device 10 may include a push-button switch 160 configured to control various functions of the device (e.g., powering the device on and off, etc.). In some aspects, the aerosol delivery device 10 may include a touchscreen that may be configured to allow a user to control functions of the device and for output of visual cues or indicia to the user. Additionally or alternatively, component(s) adapted for gesture recognition based on specified movement of the aerosol delivery device (e.g., accelerometers, gyroscopes, etc.) may be used as an actuating component such that a user can provide an input to the aerosol delivery device 10. See U.S. patent application Ser. No. 14/565,137, filed Dec. 9, 2014, to Henry et al., which is incorporated herein in its entirety by reference.

The presence of the potentiometer 162 can be useful to provide for simple, real-time temperature adjustment of the heater by a user. For example, the potentiometer 162 can be configured to work with the control component 150 to increase the heater temperature (e.g., by sliding a finger upward on the potentiometer 162) and decrease the heater temperature (e.g., by sliding a finger downward on the potentiometer 162) as desired during use of the device 10. Likewise, pre-defined positions on the potentiometer 162 can be configured to correspond to predetermined operating temperatures for the heater, and the heater temperature can be adjusted simply by touching a position on the potentiometer (e.g., higher for higher temperature and lower for lower temperature). The control component can be configured to return the heater to a defined temperature set point after a certain time period; however, the device 10 can be configured so that a user may choose a temperature as discussed above and lock the temperature (e.g., by depressing the push-button switch 160). As the user adjust temperature during use, the active temperature range can be visualized via the heating element temperature setting indicia 142 on the display unit 140.

In some aspects, an input may comprise a computer or computing device, such as a smartphone or tablet. In particular, the aerosol delivery device may be wired to the computer or other device, such as via use of a USB cord or similar protocol. The aerosol delivery device may also be configured to communicate with a computer or computing device wirelessly. See, for example, the systems and methods for controlling a device via a read request as described in U.S. patent application Ser. No. 14/327,776, filed Jul. 10, 2014, to Ampolini et al., the disclosure of which is incorporated herein in its entirety by reference. In such aspects, an application or other computer program product may be used in connection with a computer or other computing device to input control instructions to the aerosol delivery device, such control instructions including, for example, the ability to form an aerosol of specific composition by choosing the nicotine content and/or content of further flavors to be included.

Referring to FIGS. 5A and 5B, the aerosol delivery device 10 may further include a sealing element 170 disposed proximate the open end 202 of the reservoir 200. In some aspects, the sealing element 170 may be disposed within the reservoir 200. Further yet, the sealing element 170 may be disposed proximate the vaporizing orifice 108 defined by the housing 100. The sealing element 170 may be configured to sealably engage the vaporizing unit 300 when the vaporizing unit 300 is disposed in the operating position and/or coupleably engaged with the open end 202 of the reservoir 200. That is, when the vaporizing unit 300 is coupleably engaged with the open end 202 of the reservoir 200, the sealing element 170 may be configured to prevent any substantial amount of aerosol precursor composition from exiting the reservoir through the open end 202 of the reservoir 200 and/or through the vaporizing orifice 108 defined by the housing 100. Additionally, when the vaporizing unit 300 is decoupled from the open end 202 of the reservoir 200, the sealing element 170 may be configured to seal, secure, and/or otherwise substantially prevent leakage of any of the aerosol precursor composition from the reservoir 200 through the open end 202. In this manner, the open end 202 of the reservoir 200 may be considered to be "open" in that the sealing element allows for free insertion and removal of the vaporizing unit 300 even though liquid is substantially prevented from exiting therefrom. For example, the sealing element 170 may include a one-way valve configured to removably engage the vaporizing unit 300. That is, the one-way valve may be configured to retain the aerosol precursor composition within the reservoir 200 when the vaporizing unit 300 is disengaged therefrom. In some aspects, the sealing element 170 may include a membrane that includes a flexible material configured to retain the aerosol precursor composition within the reservoir 200 when the vaporizing unit 300 is removably disengaged from the sealing element 170.

According to one aspect of the present disclosure, the sealing element 170 may be further configured to engage the liquid transport element 306 and/or the outer shell 301. For example, the sealing element 170 may be configured to remove excess aerosol precursor composition from a portion of the liquid transport element 306 and/or the outer shell 301 of the vaporizing unit 300 as the portion of vaporizing unit 300 traverses the sealing element 170. As the portion of the vaporizing unit 300 traverses the sealing element 170, the sealing element 170 removes excess amounts of the aerosol precursor composition therefrom. In some aspects, the sealing element 170 may include a membrane that includes a flexible material (e.g., silicone) that removes excess aerosol precursor composition from the liquid transport element 306 and/or the outer shell 301 of the vaporizing unit 300 as it traverses the membrane. Additionally or alternatively, the sealing element 170 may include a polymer material that extends across the vaporizing orifice 108. In some aspects, when the vaporizing unit 300 engages the open end 202 of the reservoir 200, the vaporizing unit 300 penetrates the membrane as the vaporizing unit 300 extends into the reservoir 200. As the vaporizing unit 300 is removably disengaged from the open end 202 of the reservoir 200, the polymer material included in the sealing element 170 may be configured to reseal the opening caused by the vaporizing unit 300 penetrating the membrane.

Referring to FIGS. 3A and 3B, the aerosol delivery device 10 may further include a filling engaging element (180a and 180b) configured to removably and sealably engage a container for filling the reservoir 200 with the aerosol precursor composition. In some aspects, as shown in FIGS. 2 and 3A, the filling engaging element 180a may be disposed proximate the fill orifice 110 and be configured to accept aerosol precursor composition from a variety of refilling containers. Additionally, the filling engaging element 180b (see FIG. 3B) may include a structure arranged to reciprocally engage a specified refill container to ensure an authorized aerosol precursor composition stored within an authorized refill container are used to refill the reservoir 200 with the proper aerosol precursor composition. See, for example, the systems and methods for filling an aerosol delivery device as described in U.S. patent application Ser. No. 14/802,667, filed Jul. 17, 2015, to O'Brien et al., the disclosure of which is incorporated herein in its entirety by reference. Additionally or alternatively, the fill engaging element (180a and 180b) may be configured, like the sealing element 170, to prevent the aerosol precursor composition stored within the reservoir 200 from traversing the fill orifice 110. According to some aspects, the aerosol delivery device may include a single orifice (i.e., the vaporizing orifice 108) configured to engage the vaporizing unit 300 so as to produce a vapor for consumption and may be further configured to receive additional aerosol precursor composition from a refill container so as to provide the reservoir 200 with the aerosol precursor composition.

Many modifications and other aspects of the disclosure will come to mind to one skilled in the art to which this disclosure pertains having the benefit of the teachings presented in the foregoing descriptions and the associated drawings. Therefore, it is to be understood that the disclosure is not to be limited to the specific aspects disclosed herein and that modifications and other aspects are intended to be included within the scope of the appended claims. Although specific terms are employed herein, they are used in a generic and descriptive sense only and not for purposes of limitation.

The invention claimed is:

1. An aerosol delivery device comprising:
   a housing;
   a reservoir having an open end and an opposing closed end, the reservoir configured to retain an aerosol precursor composition therein;
   an electrical contact in or on the housing; and
   a vaporizing unit including:
      a liquid transport element;
      a heating element; and
      an electrical connector;
   the vaporizing unit being configured to removably engage the open end of the reservoir such that the liquid transport element is in an arrangement with the reservoir to transfer the aerosol precursor composition from the reservoir to the heating element and configured to engage the electrical contact in or on the housing;
   wherein the housing defines a fill orifice that is in fluid communication with the open end of the reservoir.

2. The aerosol delivery device of claim 1 further comprising:
   a power source disposed within the housing, the power source configured to provide an electrical current to the heating element when the vaporizing unit is engaging the open end of the reservoir and disposed in an operating position; and
   a mouthpiece coupleably engaged with the vaporizing unit.

3. The aerosol delivery device of claim 2, wherein the mouthpiece is in electrical connection with the power source when the mouthpiece is coupleably engaged with the vaporizing unit and the vaporizing unit is engaged with the open end of the reservoir, the power source being further configured to provide an electrical current to the heating element when the mouthpiece is coupleably engaged with the vaporizing unit disposed in the operating position.

4. The aerosol delivery device of claim 2, wherein the vaporizing unit includes an outer shell, the outer shell defining an aperture proximate a first end of the outer shell and an annular channel proximate an opposing second end of the outer shell, the heating element and the liquid transport element being disposed within the outer shell.

5. The aerosol delivery device of claim 4, wherein the housing further comprises an engaging element, the engaging element configured to operably engage the annular channel when the vaporizing unit is disposed in the operating position.

6. The aerosol delivery device of claim 5, wherein the engaging element includes the electrical contact.

7. The aerosol delivery device of claim 4, wherein the mouthpiece coupleably engaged with the vaporizing unit is in electrical connection with the power source when the electrical connector of the vaporizing unit is engaged with the electrical contact in or on the housing.

8. The aerosol delivery device of claim 4 further comprising a sealing element disposed proximate the open end of the reservoir, the vaporizing unit being sealably engaged with the sealing element when the vaporizing unit is disposed in the operating position, the sealing element configured to retain the aerosol precursor composition within the reservoir when the vaporizing unit is removably disengaged from the open end of the reservoir.

9. The aerosol delivery device of claim 8, wherein the sealing element is configured to remove excess aerosol precursor composition from the vaporizing unit as the vaporizing unit traverses the sealing element and is removably disengaged from the open end of the reservoir.

10. The aerosol delivery device of claim 1, wherein the fill orifice includes a filling engaging element configured to removably and sealably engage a container for filling the reservoir with the aerosol precursor composition.

11. An aerosol delivery device comprising:
   a housing including a reservoir, the reservoir configured to retain an aerosol precursor composition therein;
   a removable vaporizing unit configured to engage the reservoir;
   a mouthpiece coupleably engaged with the vaporizing unit;
   a power source;
   a liquid transport element; and
   a heating element;

wherein the housing, vaporizing unit, and the mouthpiece collectively form an electrical circuit; and wherein the power source is configured to provide an electrical current to the heating element through the electrical circuit when the housing, vaporizing unit, and the mouthpiece are coupleably engaged with one another.

12. The aerosol delivery device of claim 11 further comprising at least one electrical contact in or on the housing, the electrical contact being in electrical connection with the electrical circuit.

13. The aerosol delivery device of claim 12, wherein the mouthpiece is configured to coupleably engage the vaporizing unit to form the electrical circuit.

14. The aerosol delivery device of claim 12, wherein the mouthpiece is configured to engage at least one electrical contact to form the electrical circuit.

15. An aerosol delivery device comprising:
a housing;
an electrical contact in or on the housing;
a reservoir disposed in or on the housing, the reservoir having an open end and an opposing closed end, the reservoir defining an orifice proximate the open end configured to receive a removable vaporizing unit such that the vaporizing unit is in fluid connection with the reservoir and is in electrical connection with the electrical contact, the reservoir configured to retain an aerosol precursor composition therein;
a power source disposed within the housing, the power source being in electrical connection with the electrical contact; and
a controller disposed within the housing, the controller configured to control an electrical current provided by the power source to the electrical contact;

wherein the housing defines a fill orifice that is in fluid communication with the open end of the reservoir.

16. The aerosol delivery device of claim 15 further comprising a vaporizing unit, the vaporizing unit being configured to removably engage the open end of the reservoir such that a liquid transport element of the vaporizing unit is arranged with respect to the reservoir to transfer the aerosol precursor composition from the reservoir to a heating element within the vaporizing unit when the vaporizing unit is disposed in the operating position.

17. The aerosol delivery device of claim 16 further comprising a mouthpiece coupleably engaged with one or both of the reservoir and the vaporizing unit.

18. The aerosol delivery device of claim 17, wherein the power source is configured to provide an electrical current to the heating element and to electrically communicate with the mouthpiece when the mouthpiece is coupleably engaged with the vaporizing unit and the vaporizing unit is disposed in the operating position.

19. The aerosol delivery device of claim 17 further comprising an engaging element within the housing, the engaging element configured to operably engage an annular channel defined by an outer shell of the vaporizing unit when the vaporizing unit is disposed in the operating position.

20. The aerosol delivery device of claim 19, wherein the engaging element includes the electrical contact in or on the housing.

21. The aerosol delivery device of claim 15, wherein the reservoir removably engages the housing.

22. The aerosol delivery device of claim 21, wherein the reservoir is positioned adjacent an outer wall of the housing.

23. The aerosol delivery device of claim 22, wherein the outer wall of the housing includes a light source configured to illuminate the reservoir.

* * * * *